US008696952B2

(12) United States Patent
Kumacheva et al.

(10) Patent No.: US 8,696,952 B2
(45) Date of Patent: Apr. 15, 2014

(54) METHOD OF PRODUCING POLYMERIC PARTICLES WITH SELECTED SIZE, SHAPE, MORPHOLOGY AND COMPOSITION

(76) Inventors: Eugenia Kumacheva, Toronto (CA); Shengqing Xu, Toronto (CA); Zhihong Nie, Toronto (CA); Min Seok Seo, Toronto (CA); Patrick Cameron Lewis, Toronto (CA); Hong Zhang, Toronto (CA)

( * ) Notice: Subject to any disclaimer, the term of this patent is extended or adjusted under 35 U.S.C. 154(b) by 1241 days.

(21) Appl. No.: 11/587,251

(22) PCT Filed: Apr. 25, 2005

(86) PCT No.: PCT/CA2005/000627
§ 371 (c)(1),
(2), (4) Date: Jan. 16, 2008

(87) PCT Pub. No.: WO2005/103106
PCT Pub. Date: Nov. 3, 2005

(65) Prior Publication Data
US 2011/0129941 A1    Jun. 2, 2011

Related U.S. Application Data

(60) Provisional application No. 60/564,614, filed on Apr. 25, 2005.

(51) Int. Cl.
B01J 19/00    (2006.01)
C08F 2/00    (2006.01)

(52) U.S. Cl.
USPC ............. 264/4.1; 436/180; 422/129; 422/131

(58) Field of Classification Search
USPC .................. 422/100, 130, 68.1, 103, 110, 50; 264/4–4.7; 436/180; 427/483
See application file for complete search history.

(56) References Cited

U.S. PATENT DOCUMENTS 7,708,949 B2 *    5/2010    Stone et al. ................... 422/502
2002/0007869 A1 *    1/2002    Pui et al. ...................... 141/173
(Continued)

FOREIGN PATENT DOCUMENTS

CA    1 166 413    5/1984
CA    1166413    5/1984
(Continued)

OTHER PUBLICATIONS

Kawakatsu, et al., Colloilds and surfaces, 2001, vol. 189, 257-264.*
(Continued)

*Primary Examiner* — James J Seidleck
*Assistant Examiner* — S. Camilla Pourbohloul
(74) *Attorney, Agent, or Firm* — Hill & Schumacher

(57) ABSTRACT

The present invention provides a method and apparatus for producing polymeric particles with pre-designed size, shape, morphology and composition, and more particularly the present invention uses a microfluidic polymerization reactor for producing same. The present invention disclosed herein provides a process for producing polymer particles with pre-selected shapes. The method includes injecting a first fluid comprising a polymerizable constituent with a controlled flow rate into a microfluidic channel and injecting a second fluid with a controlled flow rate into the microfluidic channel in which the second fluid mixes with the first fluid, the second fluid being immiscible with the first fluid so that the first fluid forms into droplets in the microfluidic channel. The microfluidic channel has pre-selected dimensions to give droplets of pre-selected size, morphology and shape. The microfluidic channel is sufficiently long so that the droplets have a sufficiently long residence time in the channel so that they polymerize or otherwise harden into droplets of pre-selected size and shape.

48 Claims, 14 Drawing Sheets

(56) References Cited

U.S. PATENT DOCUMENTS

| | | |
|---|---|---|
| 2004/0197469 A1 | 10/2004 | Lyons et al. |
| 2005/0129580 A1 | 6/2005 | Swinehart et al. |
| 2006/0108012 A1* | 5/2006 | Barrow et al. ............... 137/806 |

FOREIGN PATENT DOCUMENTS

| | | |
|---|---|---|
| CA | 2 390 284 | 5/2001 |
| CA | 2 472 964 A1 | 7/2003 |
| CA | 2 436 804 | 2/2004 |
| EP | 0 933 384 A1 | 8/1999 |
| WO | WO 92/00335 | 1/1992 |

OTHER PUBLICATIONS

Thorsen, et al., Physical review letters, 2001, vol. 86, 4163-4266.*
Kawakatsu et al., J. "Effect of microchannel structure on droplet size during crossflow microchannel emulsificaiton" Surfactant Detergents 3, 2000, 295.*
Thorsen et al., Physical rev. lett., 2001, vol. 86, 4163-4166.*

* cited by examiner

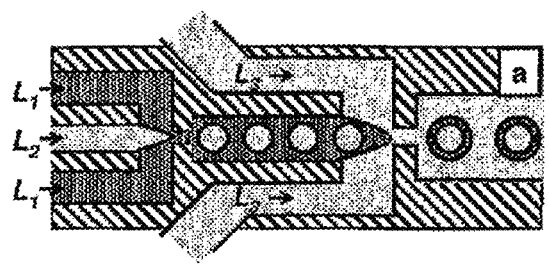
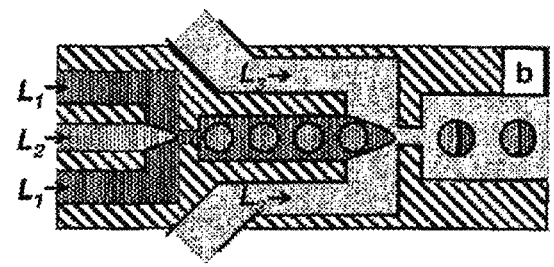
Figure 22a                    Figure 22b
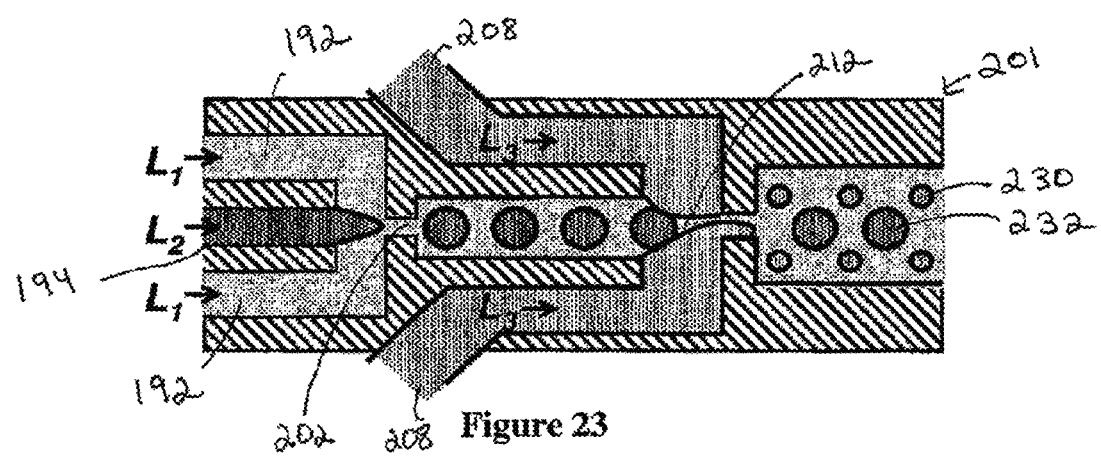
Figure 23
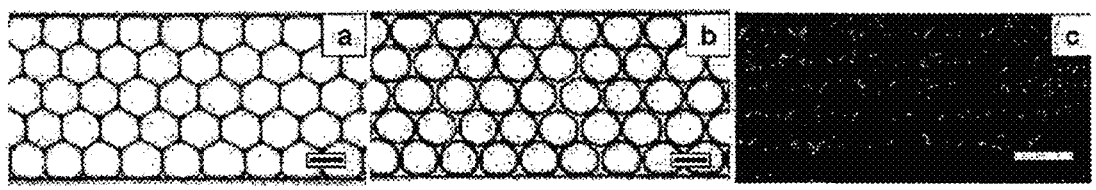
Figure 24a         Figure 24b         Figure 24c

METHOD OF PRODUCING POLYMERIC PARTICLES WITH SELECTED SIZE, SHAPE, MORPHOLOGY AND COMPOSITION

CROSS REFERENCE TO RELATED U.S. PATENT APPLICATIONS

This patent application is a National Phase application claiming the benefit of PCT/CA2005/000627 filed on Apr. 25, 2005; which further claims the priority benefit from U.S. Provisional Patent Application Ser. No. 60/564,614 filed on Apr. 23, 2004 in English entitled METHOD OF PRODUCING POLYMERIC MATERIALS WITH SELECTED SHAPE AND COMPOSITION, which is incorporated herein in its entirety.

FIELD OF THE INVENTION

The present invention generally relates to methods, devices and systems for forming particles and, in certain aspects, to systems and methods of forming particles that are substantially monodisperse and polymeric based. In some cases, the present invention generally relates to methods for producing particles having a predetermined shape, size, morphology and/or composition, and in some cases, this invention relates to a microfluidic reactor able to produce the same.

BACKGROUND OF THE INVENTION

Polymer colloids with dimensions in the range from 5 to 1000 μm are extensively used in ion-exchange and chromatography columns, in various biological and medicinal applications, as calibration standards, toners, coatings and supports for catalysts. In many of these applications, particle size and size distribution are of key importance. The preparation of monodispersed submicrometer-size polymer beads with pre-determined surface and bulk properties is a well-established procedure. By contrast, the synthesis of larger particles with a narrow size distribution is a synthetic challenge: it is either material-specific, or time-consuming (that is, it requires several stages), or it does not provide a sufficiently narrow size distribution of the resulting particles. Moreover, control of microbead shapes in conventional polymerization reactions is generally limited to the preparation of spherical particles.

Recent progress in developing new microfabrication techniques and microreaction technologies has raised new opportunities in reaction engineering. Microreactors provide high heat and mass transfer rates, safe and rapid synthesis and the possibility of the development of new reaction pathways too difficult for conventional reactors.

Typically, the preparation of polymer particles with assistance of microfluidic methods has been accomplished via a two-stage process. In the first stage, a monomer or a liquid polymer was emulsified to obtain droplets with a narrow size distribution. In the next stage, the resulting droplets were hardened in a batch (that is, non-continuous) process.

Fluid manipulation to form fluid streams of desired configuration, dispersions, and the like, for purposes of fluid delivery, product manufacture, analysis, to give a few examples, has a well established history. For example, monodisperse gas bubbles, less than 100 micrometers in diameter, have been produced using a technique referred to as capillary flow focusing. In this technique, gas is forced out of a capillary tube into a bath of liquid, the tube is positioned above a small orifice, and the contraction of flow of the external liquid through this orifice focuses the gas into a thin jet which subsequently breaks into bubbles via capillary instability.

Microfluidics is a field involving the control of fluid flow on very small scales. Typically, microfluidic devices include very small channels, within which the fluid flows, which may be branched or otherwise arranged to allow fluids to be combined with each other, to divert fluids to different locations, to cause laminar flow between fluids, to dilute fluids, or the like. Significant effort has been directed toward "lab-on-a-chip" microfluidic technology, in which researchers seek to carry out known chemical or biological reactions on a very small scale on a "chip," or a microfluidic device. Additionally, new techniques, not necessarily known on the macro scale, are being developed using microfluidics. Examples of techniques being investigated or developed at the microfluidic scale include high-throughput screening, drug delivery, chemical kinetics measurements, as well as the study of fundamental questions in the fields of physics, chemistry, and engineering.

Microfluidic reactors show promising applications in combinatorial chemistry (where rapid testing of chemical reactions, chemical affinity, or microstructure formation are desired), biochemical and organic chemistry syntheses, rapid screening of catalysts, and synthesis of inorganic particles (e.g., silica or semiconductor quantum dots). Rapid heat and mass transfer, high yield and reproducibility lead to enhanced efficiency of existing chemical reactions and allows one to explore new reaction pathways that would be difficult in conventional reactors.

It would be very advantageous to provide a method for producing polymeric particles with pre-designed size, shape, morphology, and composition. Such particles could be used in many applications from drug delivery, cell research, flow cytometry, chromatography columns, catalysis, and calibration standards to mention just a few.

SUMMARY OF THE INVENTION

The present invention provides a process for producing polymer particles of predetermined size and/or shape, and/or morphology, comprising the steps of:

a) injecting a first fluid comprising a constituent which can harden into a microfluidic channel;

b) injecting at least a second fluid into the microfluidic channel for causing the first fluid to forms into fluidic droplets within the at least second fluid causing the fluidic droplets to flow through the microfluidic channel, the microfluidic channel being sufficiently long so that the fluidic droplets harden into particles of predetermined size and/or shape while flowing through the channel; and c) collecting the hardened particles of predetermined size and/or shape from the microfluidic channel.

The present invention also provides an An apparatus for producing polymer particles with pre-determined sizes and or shapes, comprising:

a microreactor having an input end including one or more fluid inlets inputs and a microfluidic channel, said microfluidic channel being sufficiently long so that fluidic droplets located in the microfluidic channel have a long enough residence time to polymerize within the microfluidic channel; and the microreactor being made of a suitable material such that upon injecting a fluid comprising a polymerizable constituent into the microreactor the fluid forms into droplets within the microfluidic channel.

BRIEF DESCRIPTION OF THE DRAWINGS

The microfluidic reactors produced according to the present invention will now be described, by way of example only, reference being made to the accompanying drawings, in which:

FIG. 2 show schematics of the approaches to producing polymer particles with different shapes by UV-initiated polymerization in microfluidic reactor;

FIGS. 4 show typical images of particles with different compositions;

FIGS. 12 show optical microscopy images of core-shell droplets with a controlled number of cores;

FIG. 14 show typical SEM images of polyTPGDA particles. Truncated microspheres, hemispheres, particles with a "hole," and spherical capsules.

FIG. 21 show schematics of different mechanisms of the formation of droplets in microfluidic flow-focusing device;

FIG. 22 show schematics of the formation of core-shell droplets and Janus droplets in the double-orifice microfluidic flow-focusing device;

FIG. 22a shows a schematic of the formation of core-shell droplets in the double-orifice microfluidic flow-focusing device;

FIG. 22b shows a schematic of the formation of Janus droplets in the double-orifice microfluidic flow-focusing device;

FIG. 23 shows a schematic of the formation of different populations of droplets in the double-orifice microfluidic flow-focusing device;

FIG. 24 show the optical microscopy images of close-packed lattices of monomer discoid droplets obtained in the double-orifice microfluidic device before and after polymerization.

FIG. 24a shows the optical microscopy image of a two-dimensional lattice of monomer discoid droplets obtained in the double-orifice microfluidic device FIG. 24b shows the optical microscopy image of two-dimensional lattice of discoid particles obtained by photopolymerization of droplets in FIG. 24a;

FIG. 24c shows the SEM image of two-dimensional lattice of discoid particles obtained by photopolymerization of droplets in FIG. 24a;

DETAILED DESCRIPTION OF THE INVENTION

Definitions

Figure 1A:
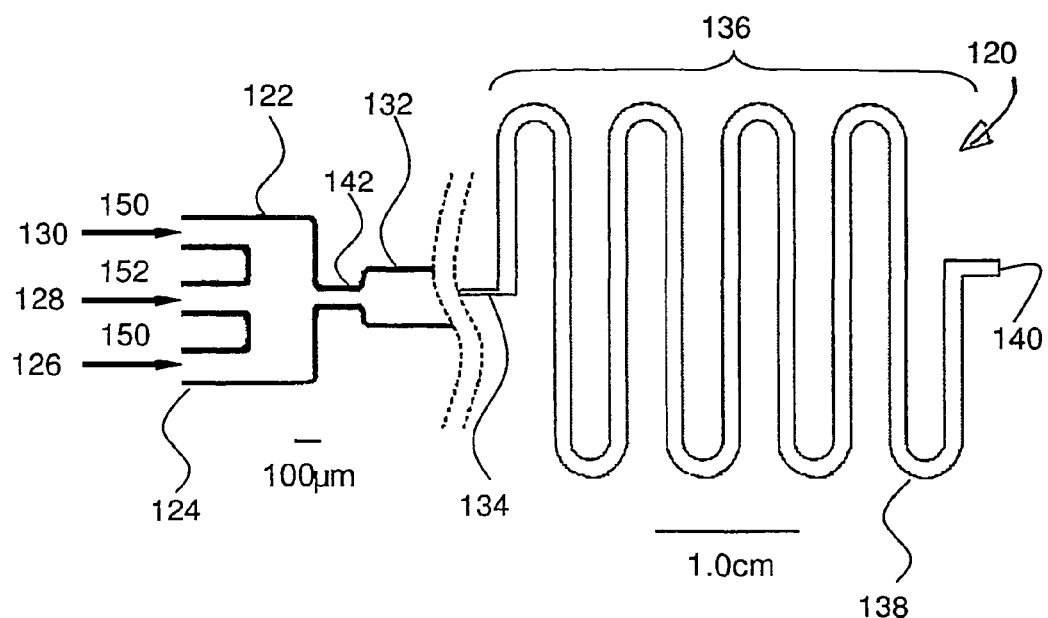
FIG. 1a shows a micrograph of the microfluidic reactor.

As used herein, the phrase "lab on a chip" means a micro device which contains microreactors and allows one to conduct efficient high yield synthesis of various compounds.

As used herein, the phrase "microreactors" means miniaturized reaction systems fabricated by using, at least partially, methods of microtechnology and precision engineering. The characteristic dimensions of the internal structures of microreactors such as fluid channels typically range from the submicrometer to the sub-millimeter range.

Some aspects of the present invention are directed to devices including one or more microfluidic components, for example, one or more microfluidic channels, which can be used to produce fluidic droplets and/or particles. As used herein, "microfluidic," refers to a device including at least one fluidic channel having a cross-sectional dimension of less than about 1 mm, and a ratio of length to largest cross-sectional dimension of the channel of at least 10:1 so that a "microfluidic channel," as used herein, is a channel meeting these criteria. The "cross-sectional dimension" of the channel is measured perpendicular to the direction of fluid flow within the channel.

As used herein, the term "channel," means a feature on or in a substrate that at least partially directs flow of a fluid. The channel can have any cross-sectional shape (circular, oval, triangular, irregular, square, or rectangular, or the like) and at least partly covered. A channel may also have an aspect ratio (length to average cross sectional dimension) of at least about 10:1.

When the term "monodisperse" is used it means the following. A particle distribution may be considered monodisperse if at least 90% of the distribution lies within 5% of the median size" (Particle Size Characterization, Special Publication 960-961, January 2001).

Microfluidic reactors use the liquid medium that is moving along the channels of the microreactors.

The present invention discloses a versatile strategy of synthesis of polymeric particles using a "lab on chip" with pre-designed size, shape, morphology, and composition. The intrinsic feature of this new approach is the ability of trapping in the solid state highly non-equilibrium shapes and morphologies of liquid droplets obtained in constrained geometry of microchannels and/or by the action of flow of the intervening medium. The inventors have demonstrated the versatility of the method by synthesizing highly monodisperse polymer microspheres with different shapes, morphologies, and structures including round spheres, elliptical beads, hemispheres, hollow particles, porous beads, core-shell particles, disks and rods.

The present invention disclosed herein provides a process for producing polymer particles with pre-selected shapes and/or size. The method includes injecting a first fluid comprising a polymerizable constituent with a controlled flow rate into a microfluidic channel and injecting a second fluid with a controlled flow rate into the microfluidic channel in which the second fluid being immiscible with the first fluid so that the first fluid forms into droplets in the microfluidic channel. The microfluidic channel has pre-selected dimensions to give droplets of pre-selected size and shape. The mixture of droplets of the first fluid in the second fluid is injected into a first input end of a longitudinal passageway sufficiently long so that the droplets have a sufficiently long residence time in the longitudinal passageway so that they polymerize into particles of pre-selected size and shape. The polymerized droplets of pre-selected size and shape are collected at a second output end of the longitudinal channel.

In the present process the polymerizable constituent is a monomer, oligomer, or liquid polymer. Alternatively, the first fluid may be a gas and the polymerizable constituent is a monomer, oligomer, or a liquid polymer.

Using the above method, the inventors have synthesized polymer and copolymer microbeads modified with fluorescent dyes, doped with inorganic nanoparticles (magnetic nanoparticles, metal nanoparticles or semiconductor quantum dots) and mixed with liquid crystals. The resulting particles can be used in their own right (e.g., in biolabeling or bioseparation) or as the building blocks in the fabrication of composite materials with periodic structure, composition and function.

Referring to FIG. 1a, a device for producing polymer particles of predetermined shape and/or size is shown generally at 120, and includes a microreactor 122 having an input end 124 which includes three separate inputs 126, 128, and 130 and an output end portion 132 which is connected to an input 134 of a microfluidic channel 136 which comprises a long tube 138. Tube 138 includes an output end 140. The length of tube 138 is sufficiently long so that fluidic droplets positioned within the microfluidic channel 136 are able to polymerize within the microfluidic channel.

Figure 1B:
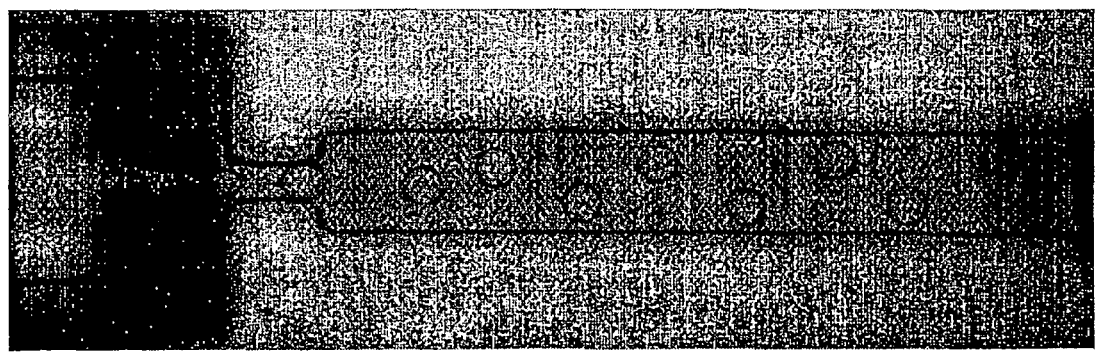
FIG. 1b shows self-focusing of monomer (liquid 2) in the orifice and the formation of monomer droplets. The intervening aqueous phase contains a dye.

The height of the channels was from 10 to 200 μm and the orifice width was from 15 to 100 μm. An aqueous solution 150 of surfactant (sodium dodecylsulphate, SDS, 2 wt %) was introduced into the outer channels 126 and 130 and a liquid monomer 152 was introduced into the inner channel 128 and using two digitally controlled syringe pumps (Harvard Apparatus PhD2000). After changing any of the flow parameters, the system was equilibrated for at least 3 min. The aqueous 150 and the monomer 152 liquids formed an interface upstream in the orifice. The tip of the monomer thread broke up in the orifice and released a monomer droplet (FIG. 1b). Monomer droplets were polymerized in a wavy microfluidic channel 138 following the downstream channel (FIG. 1a). An Olympus BX51 optical microscope with a high-speed camera, Photometrics CoolSNAR ES (Roper Scientific was used to capture images and Olympus image analysis software to measure the dimensions of monomer droplets and polymer particles.

Several nonpolar monomers tripropylene glycole diacrylate (TPGDA), ethylene glycol diacrylate (EGDMA), dimethacrylate oxypropyl dimethylsiloxane (MAOP-DMS), pentaerythritol triacrylate (PETA-3), pentaerythritol tetraacrylate, divinyl benzene (DVB) and their mixtures with other monomers or various additives were used for the formation of droplets in polyurethane microfluidic reactors.

Figure 1C:
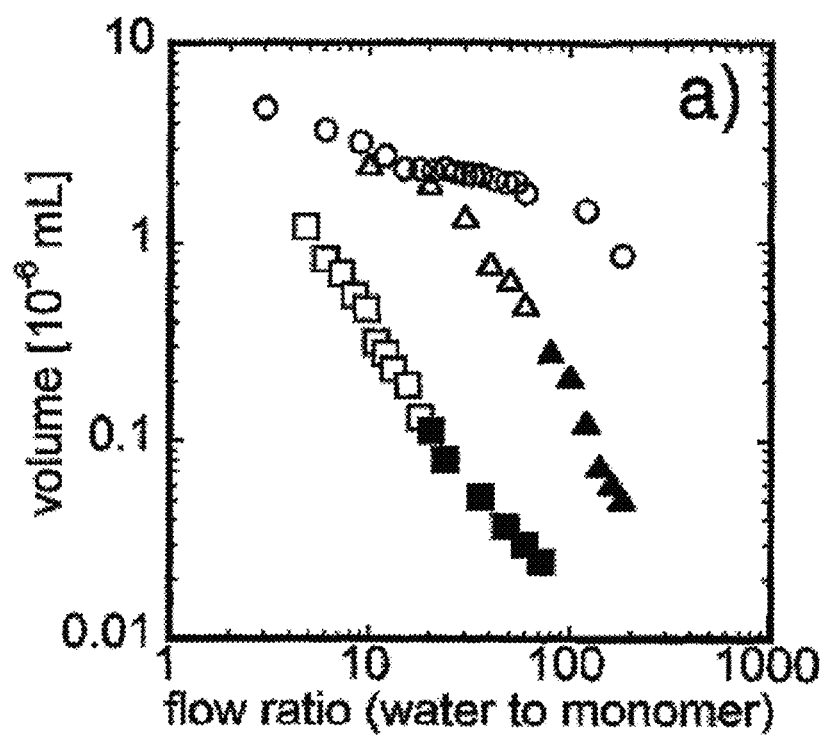
FIG. 1c shows the variation in volume of monomer droplets (styrene, methyl acrylate oxypropyldimethylsiloxane, (MAOP-DMS), and tripropylene glycol diacrylate (TPGDA) versus ratio of flow rates of aqueous phase and monomer phase. Flow rate of monomer phase is 0.04 ml/h. Open symbols correspond to disk-like droplets; filled symbols correspond to spherical droplets.
Figures 1D, 1E, 1F:
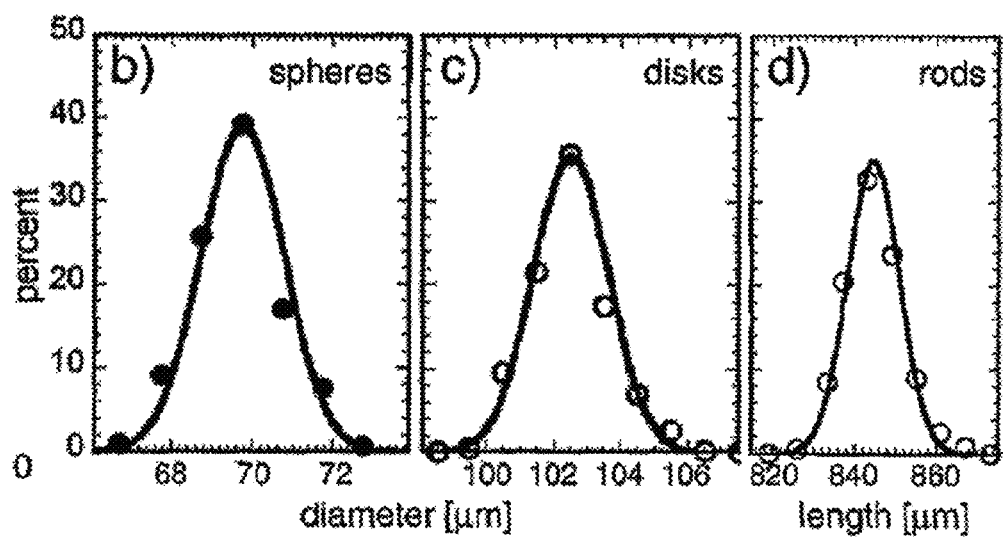
FIG. 1d shows distribution of sizes of spherical polymer particles obtained by UV-initiated polymerization of monomer droplets in microfluidic reactor.
FIG. 1e shows the distribution of discoid polymer particles obtained by UV-initiated polymerization of monomer droplets in microfluidic reactor.
FIG. 1f shows the distribution of rod-like polymer particles obtained by UV-initiated polymerization of monomer droplets in microfluidic reactor.

FIG. 1b shows highly monodisperse DVB droplets generated in the microfluidic device. FIG. 1c shows the reduction of droplet volume with increase in flow rate ratio aqueous solution/monomer phase for TPGDA, MAOP-DMS, and DVB monomers. The shape of droplets also depended on flow rate ratio: when the flow rate did not exceed 50-60, disk-like droplets formed (that is, their diameter exceed the height of microfluidic channel) (empty symbols in FIG. 1c) while at high flow rate ratios spherical droplets were obtained (filled symbols). The disk volume depended on macroscopic properties of monomers (viscosity and interfacial tension of monomers with water phase); for high flow ratios, however, this difference was less important. Several locations of droplet formation were observed in which droplets with different sizes and polydispersity were formed: in the orifice (medium flow rates of the liquids, formation of medium-size droplets); behind but close to the orifice (low flow rates, slow formation of large droplets in the "dripping" regime), and behind and far from the orifice ("jet" regime, fast formation of small droplets).

Highly monodisperse droplets were produced in this example in the range of flow rates of monomer phase from 0.01 ml/h to 0.35 ml/h. On the basis of these results, for a particular geometry of the microfluidic device (channel width and shape, height and width of the orifice), the surface energy of the mold monomer droplets with a particular size and monodispersity could be produced.

UV-initiated polymerization of monomer droplets (UVAPRINT 40 C/CE, Dr. K. Hönle GmbH UV-Technologie, Germany, λ from 330 to 380 nm, 400 W). A UV-initiator photoinitiator 1-hydroxycyclohexyl phenyl ketone, was introduced in the monomer in concentration (3.5±0.5 wt. %). Only a wavy microchannel (FIG. 1a) was exposed to UV-irradiation. The time of polymerization was controlled by droplet flow rate: typically, it was from 3 to 800 s and the rate of particle production was 250 particles/s. Microbeads with dimensions from 15 to 200 μm were collected at the outlet in aqueous solution (the dimensions of microspheres could be further reduced by changing microchannel geometry). Monomer conversion was close to 100%.

In situ polymerization prevented droplet coalescence and allowed for the production of monodisperse solid beads. Polydispersity of the microspheres (defined as standard deviation σ divided by average particle diameter D) did not exceed 3% (polydispersity index less than 1.005).

Figure 2A:
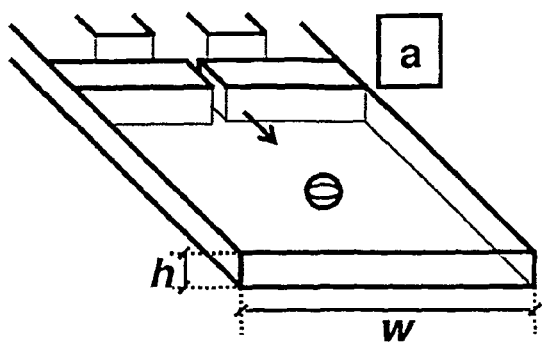
FIG. 2a shows the schematic of production of polymer microspheres.
Figure 2B:
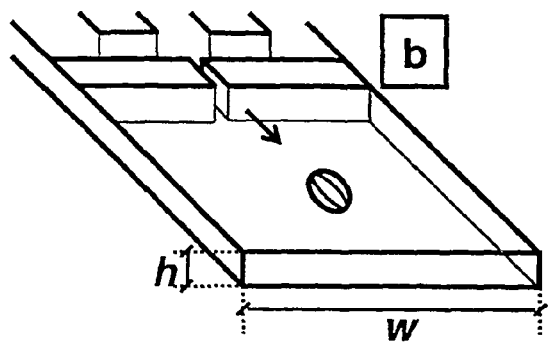
FIG. 2b shows the schematic of production of polymer ellipsoids.
Figure 2C:
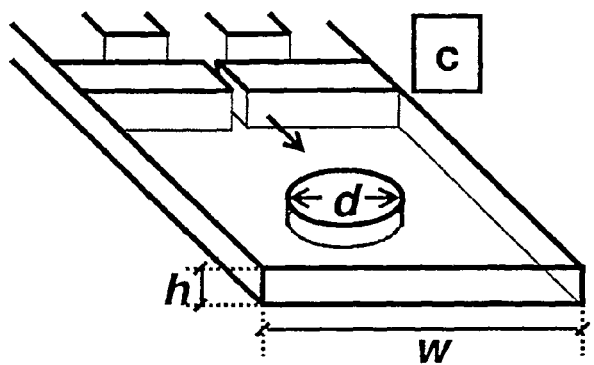
FIG. 2c shows the schematic of production of polymer disks.
Figure 2D:
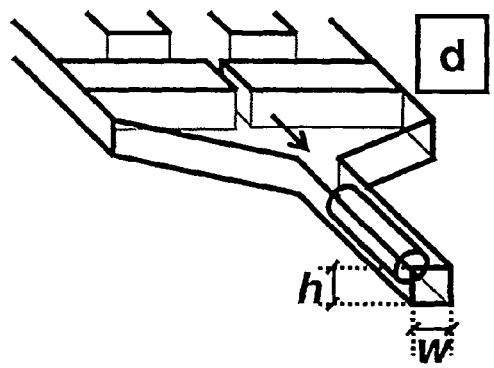
FIG. 2d shows the schematic of production of polymer rods.

FIGS. 2a to 2d show a schematic of a microfluidic reactor for production of droplets with different shapes. The relationship between the diameter (d) of an undeformed droplet and the dimensions of the channel behind the orifice (as in FIG. 1) determine the shape of droplets. Droplets with non-spherical shapes form when the value of d is larger than at least one of the dimensions of the channel. In FIG. 2a for w>d and h>d (where w and h are the width of the channel and the height of the channel, respectively) the droplets acquire a spherical shape. At high flow rates of the continuous phase the spherical droplets assume an ellipsoidal shape (FIG. 2b). For w<d and h>d the droplets assume a discoid shape (FIG. 2c) and for w<d, h<d the droplets assumed a rod shape (FIG. 2d). The aspect ratio for such non-spherical droplets could be conveniently varied by changing the ratio between droplet volume and dimensions of the microfluidic flow-focusing device.

Figures 3A, 3B, 3C, 3D, 3E:
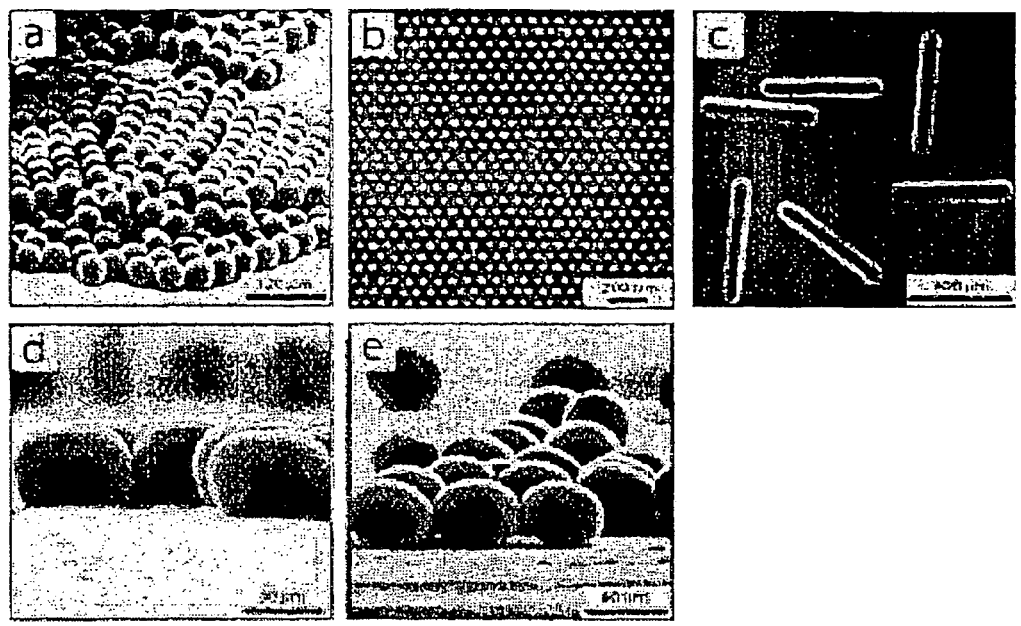
FIG. 3a shows a scanning electron microscopy image of spherical polyTPGDA particles obtained by UV-initiated polymerization in microfluidic reactor.
FIG. 3b shows typical colloid crystalline array obtained from the spherical polyTPGDA particles obtained by UV-initiated polymerization in microfluidic reactor.
FIG. 3c shows rod-like polyTPGDA particles obtained by UV-initiated polymerization in microfluidic reactor.
FIG. 3d shows discoid polyTPGDA particles obtained by UV-initiated polymerization in microfluidic reactor.
FIG. 3e shows ellipsoid polyTPGDA particles obtained by UV-initiated polymerization in microfluidic reactor.

Referring to the schematic of FIG. 2, FIG. 3(a, c-e) shows typical SEM images of particles with different shapes (spheres, rods, disks, and ellipsoids). The shapes of droplets were trapped in the solid state in the serpentine channel of the microfluidic reactor (FIG. 1a). Microspheres, disks and rods were highly monodisperse (FIG. 1(d-f). High monodispersity of polymer microspheres allowed for the formation of colloid crystals (FIG. 3(b)). The volume of particles was slightly (ca. 5-7%) smaller that the volume of the corresponding droplets, which prevented particle clogging in the serpentine channel.

The relative flow rate of the droplets in the microfluidic channel was the second factor controlling particle shape. For example, at a flow rate of the water phase 0.96 cm/s (flow ratio 8.3), the spherical droplets transformed into ellipsoids and the resulting microbeads had an "egg-like" structure (FIG. 3b). Similarly, disks could be transformed into elliptical disks.

Figures 4A, 4B, 4C, 4D, 4E:
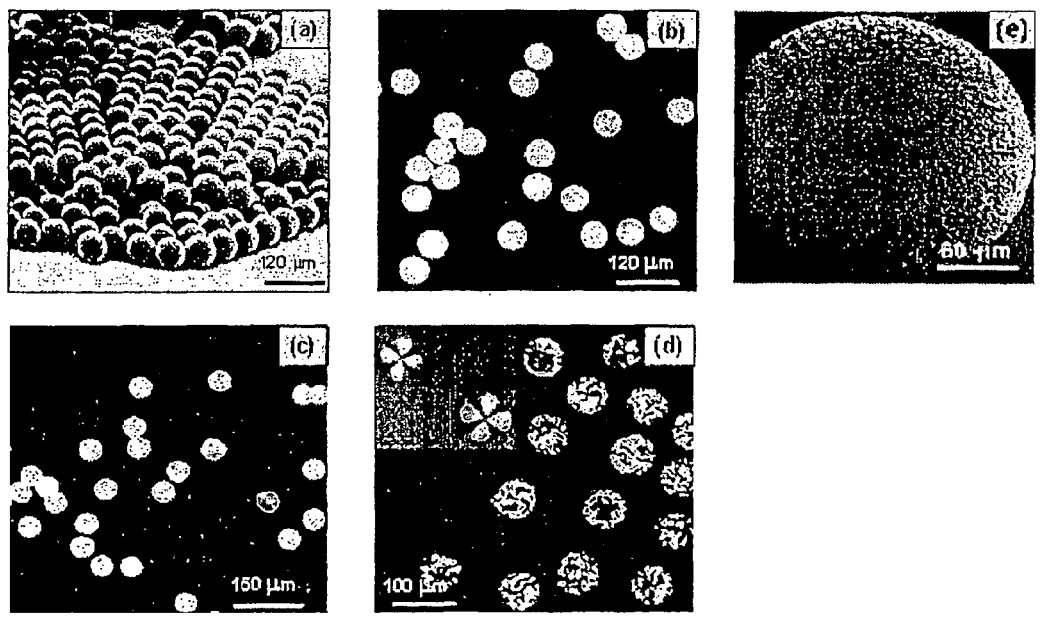
FIG. 4a is a scanning electron microscopy image of poly-TPGDA particles.
FIG. 4b is an optical fluorescent microscopy image of polyTPGDA particles labeled with 4-amino-7-nitrobenzo-2-oxa-1,3-diazole (NBD) fluorescent dye, $\lambda_{exc}$=488 nm.
FIG. 4c is an optical fluorescent microscopy image of polyTPGDA particles mixed with CdSe quantum dots, $\lambda_{exc}$=454 nm.
FIG. 4d is a polarization microscopy image of microspheres comprising polyTPGDA mixed with liquid crystal 4-cyano-4'-pentylbiphenyl (5 CB). Inset shows polymer-liquid crystalline microbeads with a core-shell morphology.
FIG. 4e is a scanning electron microscopy image of porous polyTPGDA particles.

FIG. 4 shows a typical SEM image of spherical polyTPGDA microspheres with different compositions polymerized in the microfluidic reactor. The diameter of polymer particles was from 15 to 200 μm and it could be further changed by changing microreactor design and/or hydrodynamic conditions of droplet generation. Dye labeled polymer particles were synthesized by copolymerizing UV, visible or near-IR dye-labeled monomers with the hosting monomer (Pham, H.; Gourevich, I.; Oh, J. K.; Jonkman, J. E. N.; Kumacheva, E.; A Multidye Nanostructured Material for Optical Data Storage and Security Data Encryption. *Advanced Materials* 16, 516-520 (2004). FIG. 2b shows an optical fluorescent microscopy image of microspheres produced by copolymerization of 0.01% of a fluorecent dye-labeled monomer, 4-amino-7-nitrobenzo-2-oxa-1,3-diazole methyl methacrylate (NBD-MMA), with TPGDA. (Kalinina, O.; Kumacheva, E.; A "Core-Shell" Approach to Producing 3D Polymer Nanocomposites. *Macromolecules* 32, 4122-4129 (1999). Furthermore, hybrid polymer-inorganic microbeads were obtained by polymerizing a TPGDA mixed with semiconductor, metal or magnetic nanoparticles. FIG. 4c shows an optical fluorescence microscopy image of microspheres doped with 0.3 ppm of 4.0 nm-size CdSe quantum dots capped with a mixture of tri-n-octylphosphine and tri-n-octylphosphine oxide (Murray, C B., D J Norris, M G Bawendi, *J. Am. Chem. Soc.* 1993, 115, 8706). Liquid crystal (LC)-polymer composite microbeads were synthesized by polymerizing TPGDA mixed with of 4-cyano-4'-pentylbiphenyl (5-20 wt %. FIG. 4d shows a polarization microscopy image of the LC-polymer beads. When polymerization was fast, low molecular crystal was uniformly mixed with polyTPGDA, however, when polymerization (or droplet flow rate) was slow LC segregated into the microsphere core and a polymer formed a shell (FIG. 4d, inset). TEM imaging showed that the nanoparticles remained well-separated in polymer beads and more important, as shown in FIG. 4c, maintained their fluorescence in a polymer matrix. Porous microspheres were synthesized by mixing dioctyl phalate (DOP) with TPGDA (¼ wt. ratio), polymerizing TPGDA and then removing DOP with acetone. In FIG. 4e the size of pores in a microsphere is ca. 0.90 µm.

Copolymer particles were synthesized by copolymerization of different monomers. For example, microspheres carrying carboxyl or amino groups (important for further bioconjugation) were obtained by copolymerizing TPGDA with acrylic acid (AA) or amino acrylates, respectively.

The amount of carboxylic groups on the surface of copolymer microbeads was sufficient for the immobilization of biomolecules. Bioconjugation of poly (TPGDA-AA) particles synthesized in the microfluidic reactor was demonstrated for Bovine Serum Ablumin covalently labeled with a fluorescein isothiocynate (FITC-BSA). The bioconjugation was achieved by first, attaching the FITC-BSA to the polymer particles for 1 h at 30° C. by in a phosphate buffer at pH=6.0. Following this step, 1-ethyl-3-(3-dimethylaminopropyl)carbodiimide hydrochloride was added to the dispersion of poly (TPGDA/AA) microbeads bearing FITC-BSA; the system was then mixed for 1 h at 30° C. After sonicating and sedimenting the resulting microbeads, we re-suspended them in deionized water. A series of control experiments was conducted to prove that FITC-BSA attached to the microbead surface: we heated microbeads with (i) FITC-BSA, (ii) EDC and (iii) EDC and FITC-BSA. Attachment of fluorescent FITC-BSA to the microbead surface occurred only in case (iii).

Other inorganic chemicals such as inorganic pigments may be incorporated into the polymerizable liquids fluids so that they are incorporated into the final particles. The fluids may also contain inorganic particles having pre-selected magnetic properties, or inorganic particles having pre-selected electrical and/or semiconducting properties, or inorganic particles having desired electrically conductive properties so that these types of particles are incorporated into the polymer particles of pre-selected size, composition, morphology and shape.

The final particles may also have carbon nanotubes incorporated therein. In addition, polymer particles may be produced having unpolymerizable liquids incorporated into the polymerizable fluids so that liquids are incorporated into the particles. For example, the unpolymerizable liquid may be a liquid crystal.

The particles may be produced containing biocompatible products like starch, polymers containing 3-hydroxybutyrate and its derivatives, polymers containing 3-hydroxyvalerate and its derivatives, proteins, nucleic acids (DNA, RNA), amino acids, peptides, liposomes, phosphate, polysaccharides, drugs and their derivatives that incorporated into the polymerizable fluids.

An external field may be applied to the droplets in the microfluidic device to change droplet shape and composition. The external field may be a magnetic field, an electric field, light or some other form of radiation.

The fluids of continuous phase/matrix may be water, an aqueous solution of inorganic chemicals or surfactants or polymers or other organic chemicals, or nonpolar oil liquid, e.g., oil or an oil solution of surfactants or polymers. The monomer or oligomers may be vinyl-containing monomer with one or more vinyl groups, acrylate-containing monomer with one or more acrylate groups, amide-containing monomer with one or more amide groups. The fluids may contain reactive chemicals, that will lead to reaction on the interface between the two fluids. The polymerization of fluids in the tube may be carried out by chemical reactions, UV or plasma irradiation, or by the application of electric field.

Figure 5:
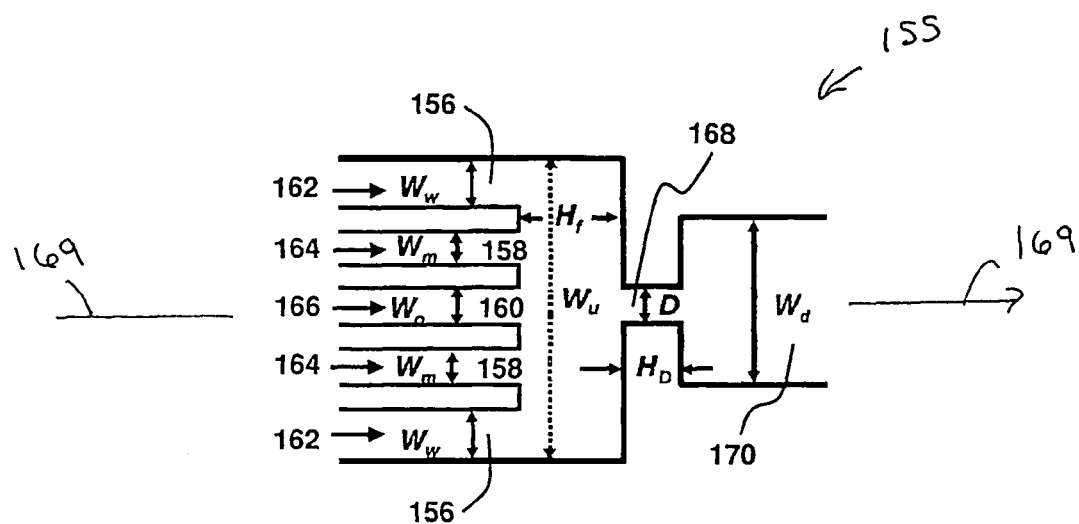
FIG. 5 shows a fragment of a microfluidic device used to produce core-shell or multi-core particles and particles with different shapes.
Figure 6:
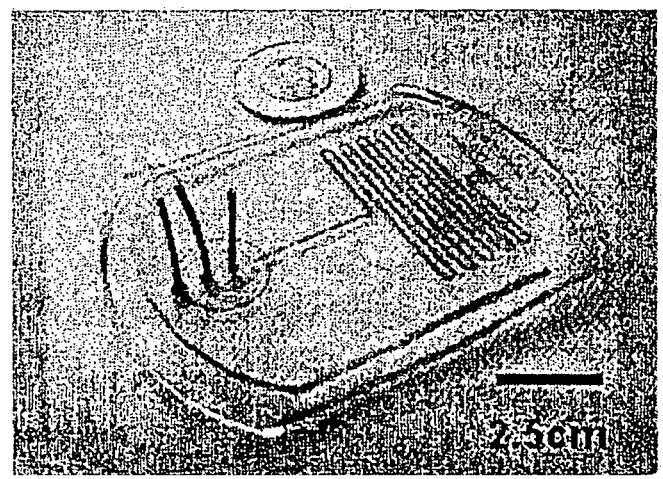
FIG. 6 shows an optical microscopy image of the microfluidic reactor used to produce core-shell or multi-core particles and particles with different shapes.

FIG. 5 shows at 155 schematic of a fragment of another embodiment of a microfluidic reactor used for the production of polymer capsules or core/shell structures and particles with non-symmetric shapes. FIG. 6 shows an optical microscopy photograph of the whole microfluidic reactor whose fragment is shown in FIG. 5. In FIG. 5 three liquids A, B, and C are supplied to the microfluidic flow-focusing device. It is important that the neighboring liquids are immiscible and at least one of them, e.g., liquid B contains the polymerizable constituent. The typical examples of the liquids used were water, monomer, and oil liquids. Typically, a 2 wt % aqueous solution of sodium dodecylsulfate (Liquid C) 162 is injected into the two outer passageways 156, the monomer phase (Liquid B) 166 and oil (Liquid A) 164 are injected into the inner channels.

Figure 7:
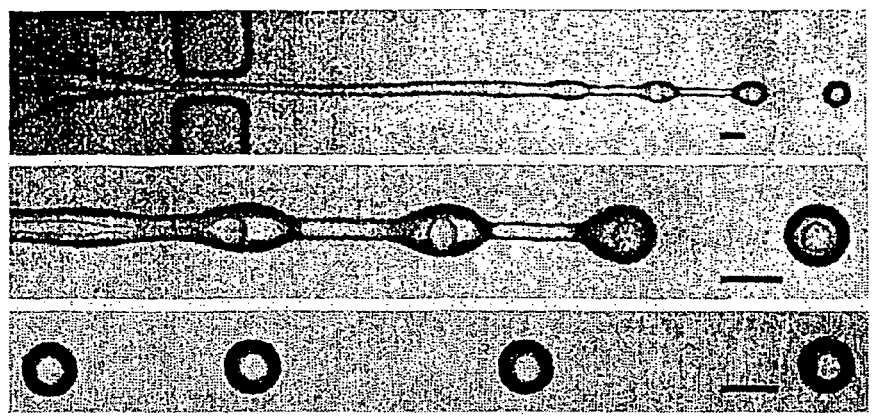
FIG. 7 shows optical microscopy images of the formation of core-shell droplets.

When a pressure gradient acting along the long axis 169 of the microfluidic device 155 forces three liquids into a narrow orifice 168 the monomer stream 164 is pulled away from the top and bottom walls of the PU mold, due to the higher affinity of the water phase 162 to the PU elastomer and strong contraction of highly accelerating external phase. Thus the continuous water phase surrounds the monomer-oil thread which adopts a circular cross-section. The coaxial oil-monomer jet extends into the downstream channel and brakes up into segments. Under the action of interfacial tension these segments acquire a spherical shape and form core-shell droplets (FIG. 7). The monomer compartment in these droplets is polymerized by exposing them to UV-irradiation in the wavy microfluidic channel (FIG. 6).

Figure 8A:
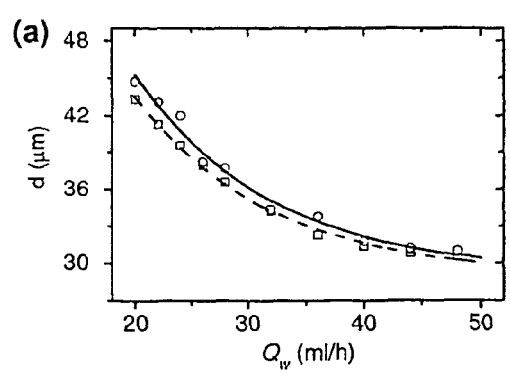
FIG. 8a shows experimental (o) and calculated (□) variation in average diameter of the coaxial oil-monomer jet plotted as a function of flow rate of the continuous phase.
Figure 8B:
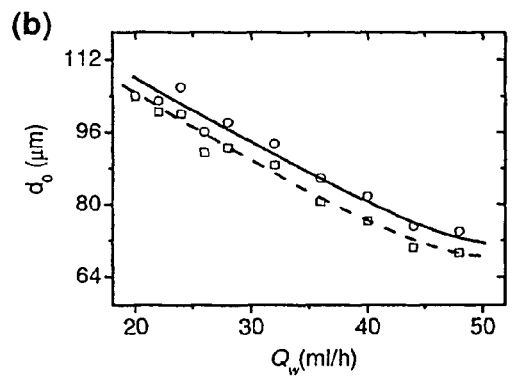
FIG. 8b shows experimental (o) and calculated (□) average diameter of core-shell droplets plotted as a function of flow rate of the continuous phase.

In this example the generation of droplets from a liquid cylindrical jet occurred due to Rayleigh-Plateau hydrodynamic instability: under the action of interfacial tension the jet became unstable to perturbations with wavelengths larger than its circumference and reduced its surface area by breaking-up into segments that acquired a spherical shape. The average diameter of the coaxial jet, d, in the equilibrium region was calculated using the continuity equation as $d=[(4/\nabla)(Q_{drop}/v_{x,\,cont})]1/2$ (1) where $v_{x,\,cont}$ is the velocity of the continuous phase in the center of the channel, $v_{x,\,cont}=1.5 Q_{cont}/A_{channel}$, $Q_{drop}$ and $Q_{cont}$ are the flow rates of the droplet and continuous phases, respectively, and $A_{channel}$ is the area of cross-section of the downstream channel. The diameter, $d_o$, of droplets generated by break-up of the jet was determined by the value of interfacial capillary wavelength, □breakup, as $d_0=(1.5\lambda_{breakup}\,d^2)^{1/3}$ (2) where interfacial capillary wavelength is the length of the last wave within the coaxial jet before it broke up into droplets. FIG. 8 shows the variation in jet diameter and the diameter of core-shell droplets with increasing flow rate of the continuous aqueous phase (the flow rates of monomer and oil phases were constant). The average diameter of the coaxial jet varied from 10 to 80 µm, in agreement with values of d calculated from equation (1) (FIG. 8, top). The average diameter of the core-shell droplets varied from 20 to 150 µm (FIG. 8, bottom), close to the values of $d_o$ obtained from equation (2).

Figure 9:
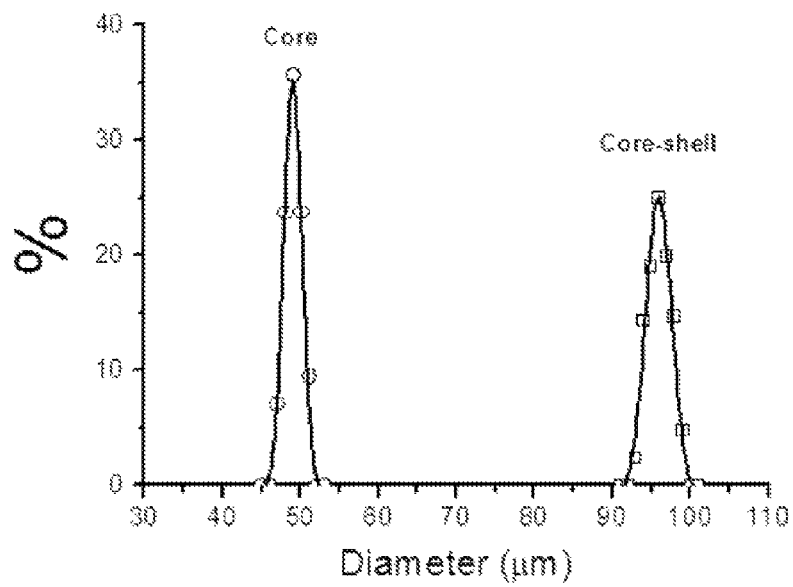
FIG. 9 shows distribution of sizes of cores of droplets and core-shell droplets obtained in the microfluidic flow-focusing device.
Figure 10A:
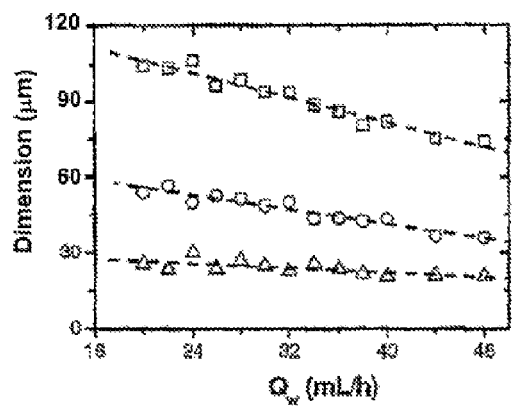
FIG. 10a shows variation in diameters of cores (o), core-shell droplets (□) and shell thicknesses (Δ) as a function of water flow rate.
Figure 10B:
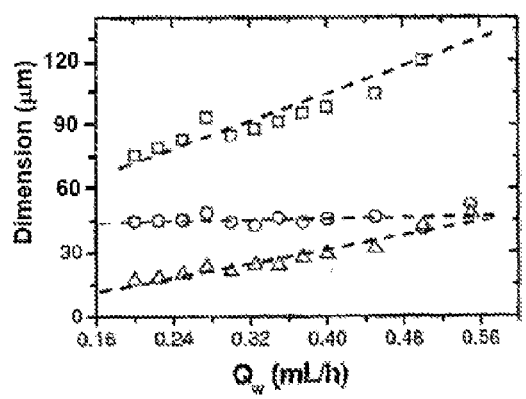
FIG. 10b shows variation in diameters of cores (o), core-shell droplets (□) and shell thicknesses (Δ) as a function of monomer flow rate.
Figure 10C:
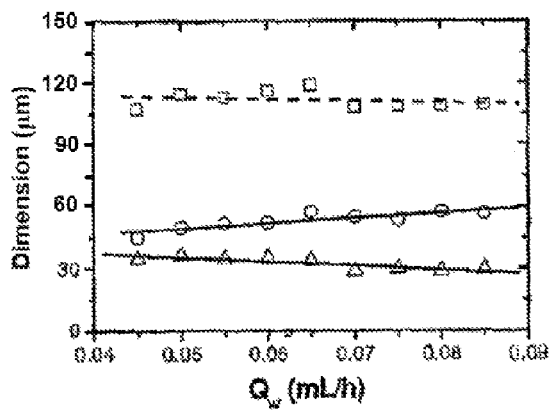
FIG. 10c shows variation in diameters of cores (o), core-shell droplets (□) and shell thicknesses (Δ) as a function of oil flow rate.

Both the cores of droplets and the core-shell droplets had very high monodispersity (FIG. 9). The size of cores, the thickness of shells, and the size of core-shell particles could be precisely controlled by changing the flow rate of one liquid while keeping the flow rates of two other liquids invariant (FIG. 10).

Figure 11:
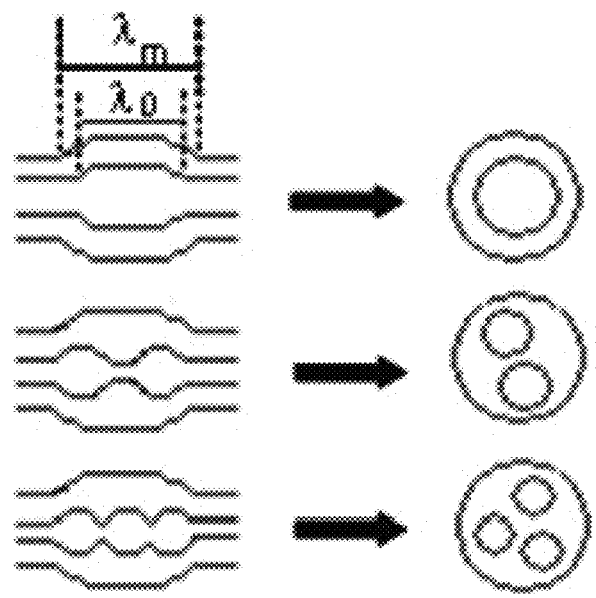
FIG. 11 shows a schematic of formation of core-shell droplets with a controlled number of cores.

FIG. 11 shows a schematic of the approach to droplets with multiple cores. The number of cores per droplet was controlled by changing the relative flow rates of the liquids: we varied the values of interfacial capillary wavelengths $\lambda_m$ and $\lambda_o$ and shifted the phases of the capillary waves (undulations) with respect to each other. In this manner, we produced core-shell droplets with a different number, n, of cores. When the values of interfacial capillary wavelengths, $\lambda_m$ and $\lambda_o^{29}$ of the monomer and oil threads, respectively, were close and "in-phase", break-up of the coaxial jet produced droplets with a single oil core localized in the center of the droplet. The core was aligned asymmetrically with respect to the droplet centre when the capillary wavelengths were "shifted in phase"; this configuration did not relax during photopolymerization.

Figures 12A, 12B, 12C, 12D:
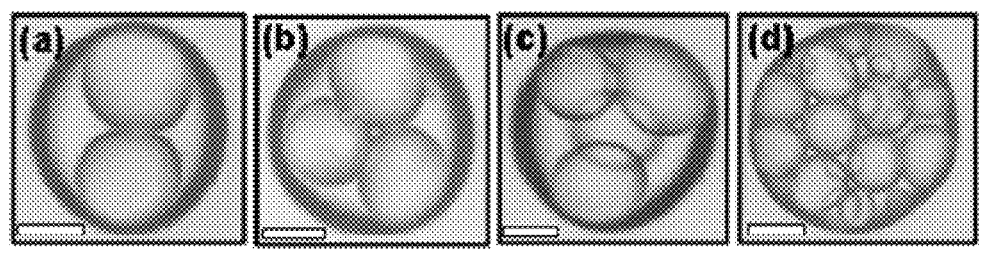
FIG. 12a shows a core-shell droplet with two cores.
FIG. 12b shows a core-shell droplet with three cores.
FIG. 12c shows a core-shell droplet with four cores.
FIG. 12d shows a core-shell droplet with multiple cores.
Figure 12E:
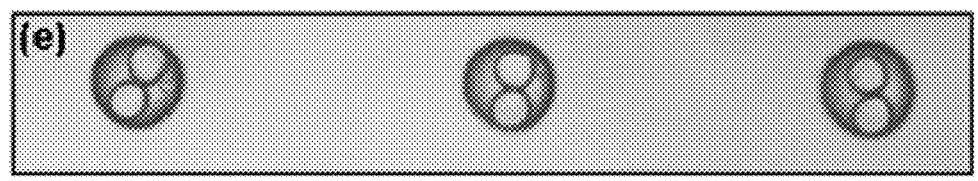
FIG. 12e shows core-shell droplets with two cores flowing through a downstream channel of the microfluidic device.
Figure 12F:
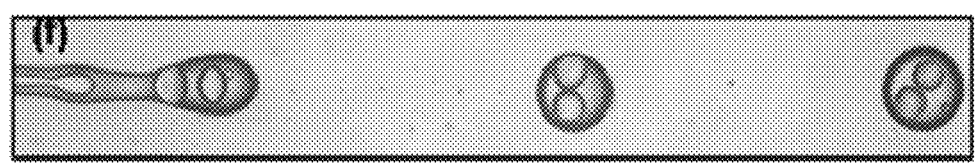
FIG. 12f shows stable formation of the core-shell droplets from a co-axial jet.

FIG. 12 shows typical optical microscopy images of the isolated monomer droplets with a different number of oil cores produced as shown in FIG. 11 and the break-up of the coaxial jet into core-shell droplets with two cores per droplet and. The fluid cores did not coalesce when they were engulfed with a monomeric shell.

Figure 13:
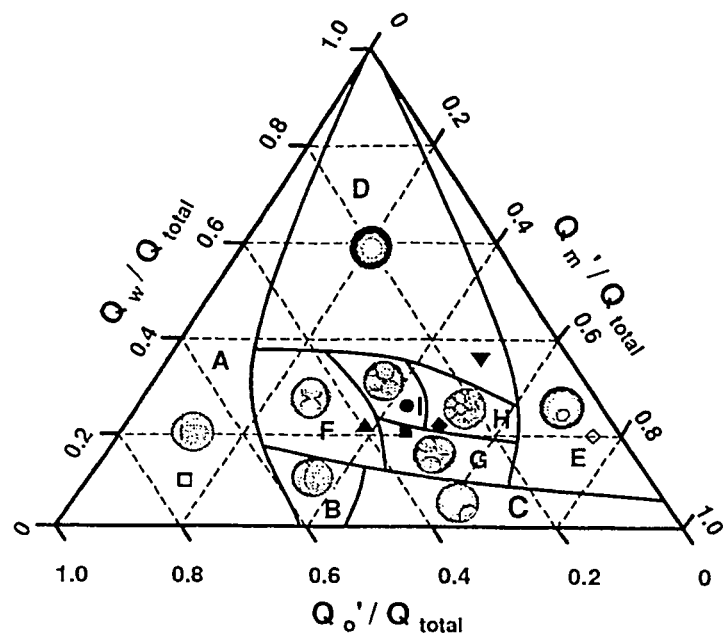
FIG. 13 shows phase-like diagram of the formation of core-shell droplets with multiple cores and droplets with different morphologies.

A ternary 'phase' diagram of hydrodynamic conditions was used for the production of core-shell droplets with different morphologies. To meet the requirement of ternary diagrams (that is, the sum of three variables is constant and equal to 1) in FIG. 13 we plotted on each axis the ratio of flow rate of a particular liquid (water, oil, or monomer phase) to the total flow rate of three liquids. We covered the whole range of flow rate ratios on the same diagram by using $Q'_o=240Q_o$, $Q'_m=120Q_m$, $Q_{total}=Q'_o+Q'_m+Q_w$ where $Q_o$, $Q_m$, and $Q_w$ are the flow rtaes of oil, monomer and water phases.

In an early stage of evolution of a monomer droplet (and after close-to-complete emergence of an oil droplet) break-up of the jet produced droplets with a small monomer inclusion adjacent the surface of oil droplet (region A). In the later stages of monomer droplet formation, the size of the monomer inclusion gradually increased (region B). Ultimately single-core droplets with classical core-shell morphologies evolved in a broad range of liquid flow rate ratios (region D). In an early stage of the evolution of an oil droplet, break-up of the jet produced droplets with a small oil inclusion adjacent the surface monomer droplet (region C). Droplet morphology was also controlled by reducing the flow rate ratio $Q'_o/Q_{total}$: under these conditions an oil core in the core-shell droplets was misaligned with respect to the droplet centre (region E). Droplets with multiple cores were obtained in regimes F-I.

Polymer particles with different shapes and morphologies were obtained by in-situ photopolymerizing a monomer in the core-shell droplets and under some conditions removing the silicone oil with acetone. The polymerization time was typically from 2 to 800 s. Conversion of monomer to polymer was close to 100%. Following polymerization the dimensions of the particles decreased by ca. 5-7%, in comparison with the corresponding droplets. No clogging of polymer particles occurred in the wavy channel. The productivity of the microfluidics reactor was from 200 to 1000 s$^{-1}$. Particle polydispersity did not exceed 2.5%, close to the polydispersity of the corresponding droplets.

FIG. 14(a-f) shows typical SEM images of polyTPGDA particles. Truncated microspheres, hemispheres, particles with a "hole", and spherical capsules (FIG. 14(a-e) were obtained from the droplets obtained in regions A, B, C, and D, respectively, of the ternary diagram in FIG. 13. Microspheres with three cores (FIG. 14f) were obtained by polymerizing droplets obtained in region 1. In our work particles with various shapes and morphologies were obtained without changing the macroscopic properties of liquids (e.g., their viscosities and interfacial tensions), by contrast with a thermodynamically-driven control of droplet morphologies.

Figure 15:
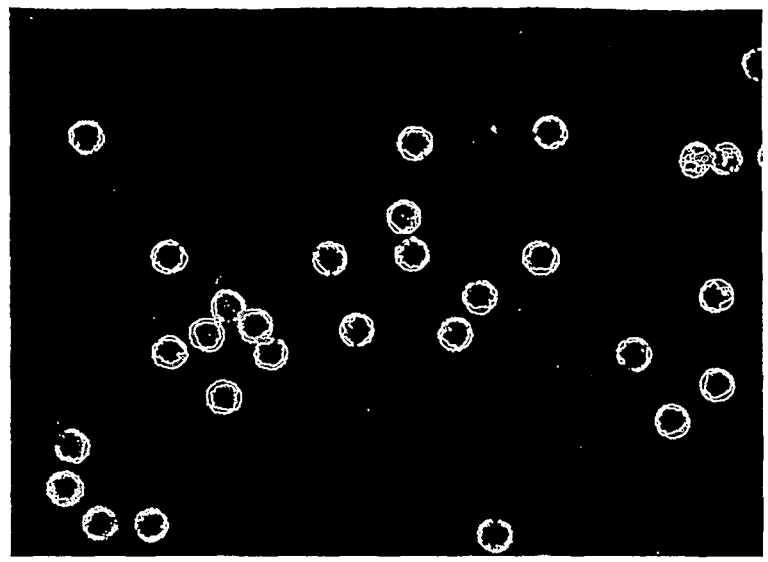
FIG. 15 shows an optical microscopy image of poly(ethylene glycol) diacrylate hydrogel particles synthesized by UV-initiated polymerization in microfluidic device with design shown in FIG. 1.

Polymer hydrogels of poly(ethylene glycol) diacrylate were obtained in a microfluidic reactor in FIG. 1. By contrast with non-polar monomers in this case the microfluidic reactor was fabricated in PDMS. A solution of surfactant Span-80 in silicone oil (viscosity 5 cSt) was introduced in the outer channels and an aqueous solution of surfactant cetyltrimethylammonium bromide, poly(ethylene glycol) diacrylate, and photoinitiator 2-hydroxy-2-methylpropiophenone was supplied into the central channel. The droplets formed after passing these liquids through the orifice. Then, poly(ethylene glycol) diacrylate in the droplets was photocrosslinked by exposing the droplets flowing through the wavy channel to the UV-irradiation. The microgel particles had polydispersity below 2% (FIG. 15).

The present invention involves the fast preparation of highly monodisperse hydrogel beads in another embodiment of the microfluidic reactor by using ionic association. The hydrogel beads are in the size range of 10 to 1000 micrometers. The size of hydrogel particles can be readily manipulated by change in concentration of solutions, flow rate and flow rate ratio of liquids, and the design of microfluidic device.

Figure 16:
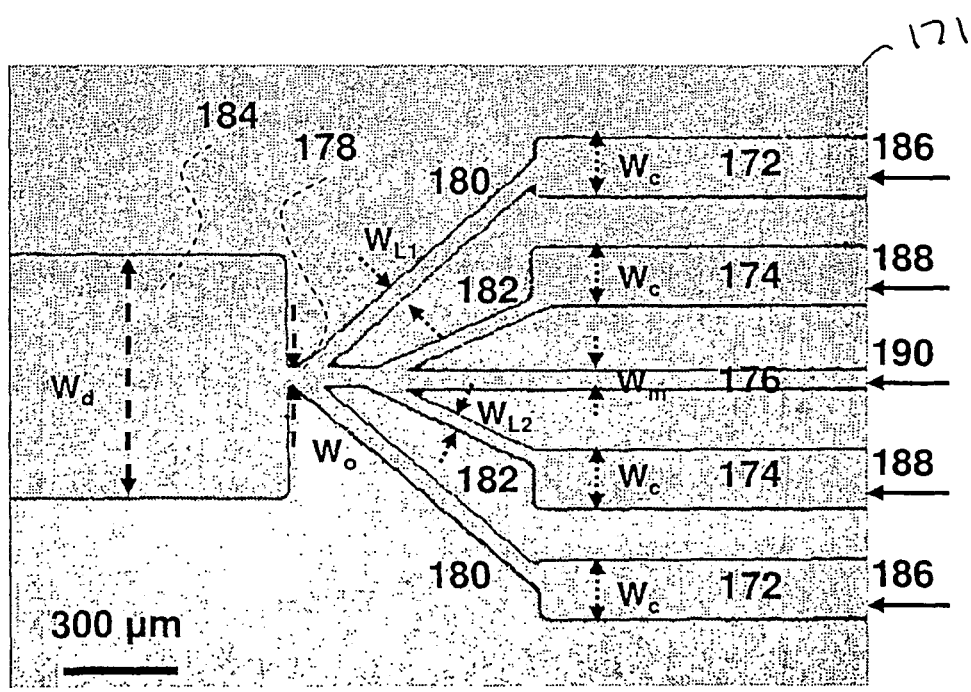
FIG. 16 shows optical microscopy image of the fragment of the optical microscopy image of the microfluidic device used for the preparation of alginate gel particles.

The exemplary materials used in the preparation of hydrogel beads are biopolymers such as proteins and polysaccharides, such as alginate and chitosan. FIG. 16 shows a schematic of a portion of a microfluidic reactor at 171. A fluid comprised of a monomer, an oligomer, or polymer or their solutions (Liquid A) 190 is supplied to the central channel 176. Typical polymers include alginate or chitosane. A solution of the crosslinking agent (Liquid B, typically, a solution of CaCl$_2$) 188 is supplied to the intermediate channels 174 on either side of channel 190. A continuous phase (Liquid C, typically, mineral oil) 186 is supplied to the outer channels 172. At the exit from the corresponding channels 182 and 176 liquids A and B mix to form a solution which, when this solution passes position 178, is sheared by liquid C exiting from channels 180 so that a mixed solution breaks up into droplets. In the downstream channel 184 these droplets gel to produce microgel beads.

Figure 17:
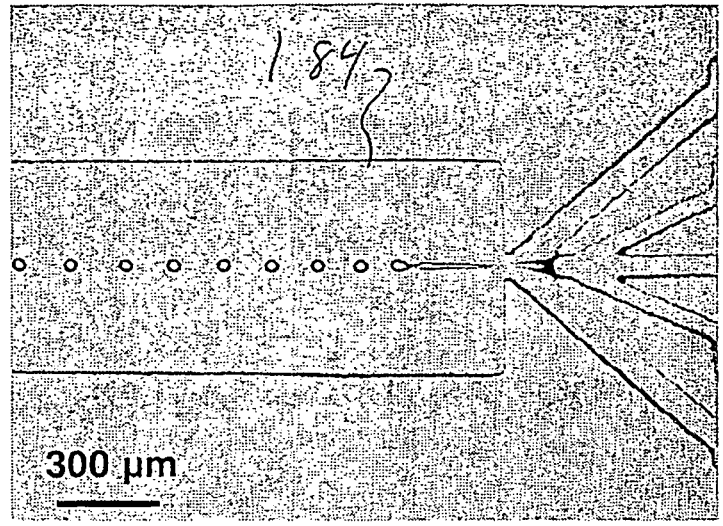
FIG. 17 shows optical microscopy image of the formation of alginate gel particles in the microfluidic device shown in FIG. 16.
Figure 18:
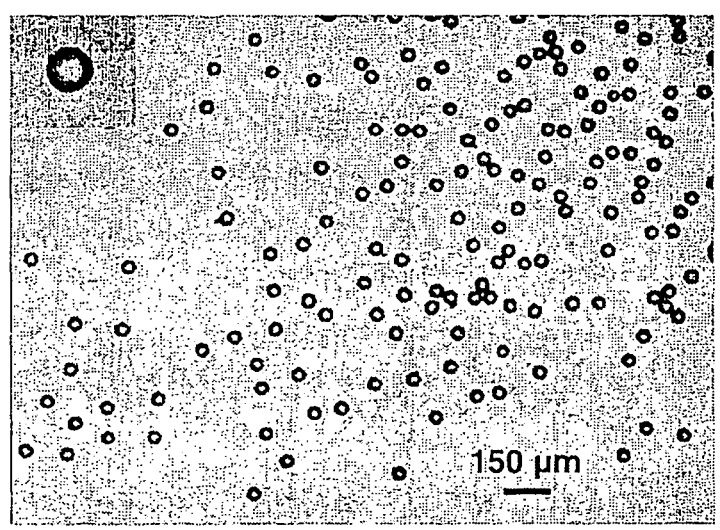
FIG. 18 shows optical microscopy image of alginate gel particles obtained in the microfluidic device shown in FIG. 16.
Figure 19:
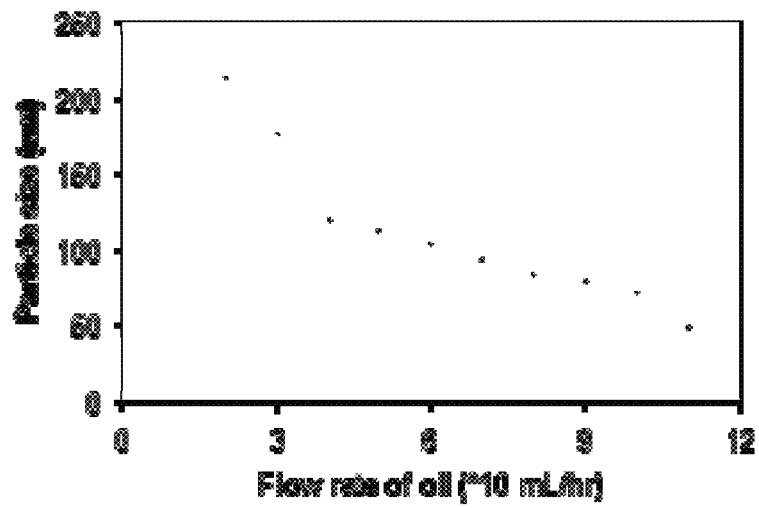
FIG. 19 shows variation in sizes of alginate gel particles shown in FIG. 18.

FIG. 17 shows the formation of microgel beads in the downstream channel 184. These microgel particles had a polydispersity of ca. 2-3% and were stable when collected at the exit of the reactor as shown in FIG. 18. The size of microgel particles was controlled by changing the flow rate of the continuous oil phase. FIG. 19 shows a plot of the particle size versus flow rate of the continuous oil phase. Typically, the diameter of the microgel particles was from about 15 to about 250 µm.

Figure 20:
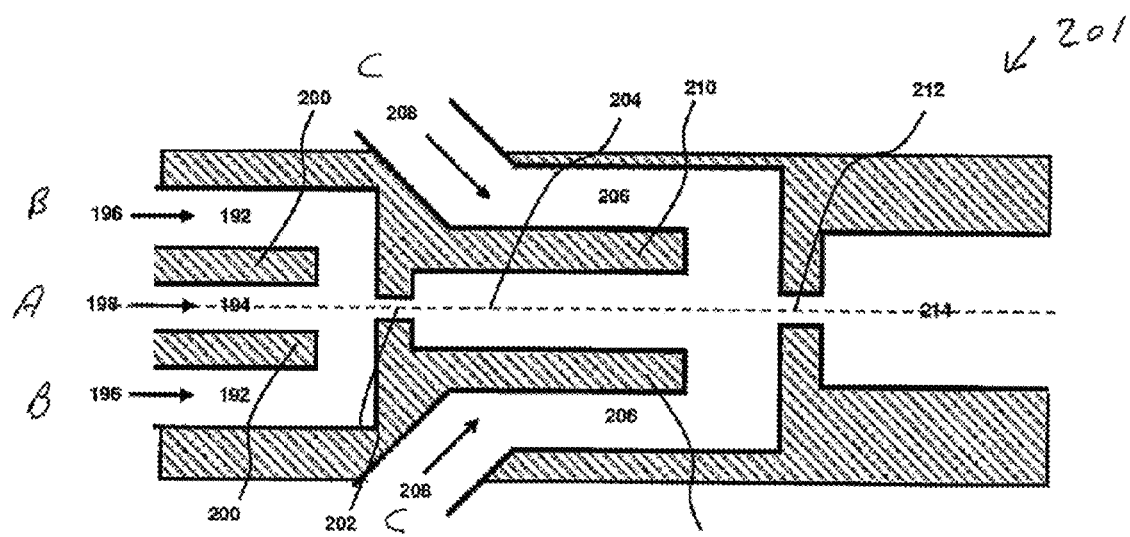
FIG. 20 shows a schematic of the double-orifice microfluidic device.

FIG. 20 is a schematic of a double-orifice microfluidic device 201. The fluids flow from left to right per the orientation of the microfluidic device. Two immiscible liquids A 198 and B 196 are supplied to the central and outer channels 194 and 192, respectively of the microfluidic device. When forced through the orifice 202 a thread of liquid A 198 forms droplets dispersed in liquid B, in a manner similar to that in FIG. 1a. Liquid C 208, which is immiscible with liquid B, is supplied from two sides of the microfluidic device through channels 206. Liquid C can be different or the same as liquid A. When liquids A, B, and C are forced through the second orifice 212 into microfluidic channel 214 liquid C forms droplets dispersed in liquid B, or liquid C becomes a continuous phase while liquid B engulfs droplets of liquid A, or liquids A and B form Janus droplets. Janus droplets or particles are made from two distinct hemispheres bound to form a sphere.

Figures 21A, 21B, 21C:
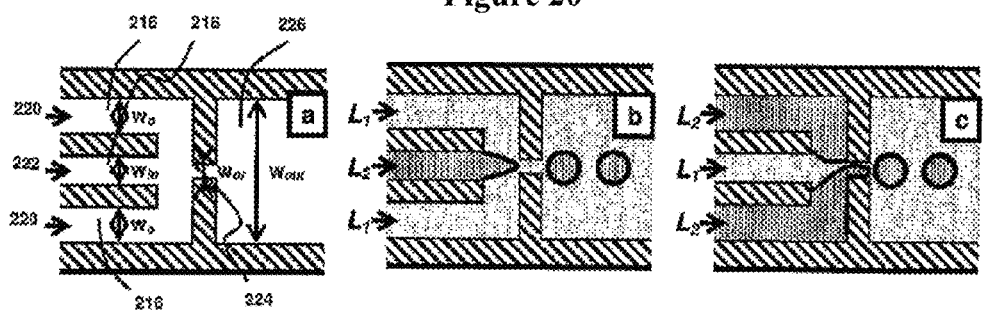
FIG. 21a shows a schematic of the fragment of the flow-focusing microfluidic device.
FIG. 21b shows a schematic of droplet formation by flow focusing of two liquid threads in the orifice.
FIG. 21c shows a schematic of droplet formation from the continuous phase by shearing it off in the orifice.

FIGS. 21a and 21b is a schematic illustration of the formation of droplets by two different mechanisms using the microfluidic reactor 120 of FIG. 1. Immiscible liquids L1 and L2 (e.g., oil and aqueous phases) are forced into the narrow orifice. FIG. 21a shows a diagrammatic representation of the generation of droplets through a flow-focusing mechanism from the liquid supplied to the central channel. In this mechanism the continuous phase supplied to the outer channels has a higher than the dispersant phase ability to wet the material of the microfluidic device. FIG. 21b is the schematic of the formation of droplets occurs by the shear-off mechanism at the corner of the orifice from the liquid supplied to the outer channels. In this mechanism the dispersant phase has a higher than continuous phase ability to wet the material of the microfluidic device.

FIG. 22a and 22b show the formation of droplets in the embodiment of the microfluidic reactor 201 in FIG. 20. In FIG. 22a liquid L3 can be the same or different as liquid L2 and should be different than liquid L1. Liquid L1 and L2 are immiscible and have moderate interfacial tension. Droplets of liquid L2 in the continuous phase of liquid L1 are formed when liquids L1 and L2 are passed through the first orifice 202. Following the injection of liquid L3, liquid L1 engulfs liquid L2 to form core-shell droplets, while Liquid L3 becomes a continuous phase. In FIG. 22b the process of droplet generation is similar to that in FIG. 22a but liquid L1 and L2 are immiscible and have high interfacial tension. Liquid L3 is different than both liquid L1 and L2. Under these conditions, liquids L2 and L3 form Janus spherical droplets composed of portions of liquid L2 and L3.

FIG. 23 shows a schematic of the formation of two populations of droplets 230 and 232 using device 201 of FIG. 20 which, depending on the selected processing conditions, can differ or be similar in size and/or in composition, or be quite different in both the size and composition. The first population of droplets 232 is generated by passing two immiscible liquids, L1 and L2, through the first orifice 202. When the liquid supplied to the central channel (L2) 194 has a lower wettability of the material of microfluidic device than the continuous phase liquid L1, supplied to the intermediate channels 192 it forms droplets dispersed in L1. This dispersion is then forced through the second orifice 212. Simultaneously, liquid L3 is supplied to the microfluidic device from the outer channels 208. If liquid L3 has a lower than L2 wettability of the material of microfluidic device it will form the second population of droplets dispersed in L1. These droplets may have the same or different size and composition as the droplets formed from L2.

FIG. 24 shows optical microscopy and SEM images of the two-dimensional lattices of droplets of dimethacrylate oxypropyl dimethylsiloxane (MAOP-DMS). An aqueous solution of sodium dodecylsulfate with concentration 2 wt % and MAOP-DMS mixed with 3.5±0.5 wt % of 1-hydroxycyclohexyl phenyl ketone were introduced into the microfluidic device (FIG. 1) fabricated in polyurethane at flow rates 0.0030 ml/hr and 0.1000 ml/hr, respectively. When the two liquids were forced through the orifice MAOP-DMS formed droplets. The flow rate of droplets was lower than the flow rate of the continuous phase and they began to pack in two-dimensional gliding lattices with a high degree of order and symmetry. Typically, the number of columns aligned parallel to the wall of the microfluidic device was up to 20. FIG. 24a shows an exemplary lattice of MAOP-DMS droplets (FIG. 24(a)). The lattice was exposed to UV-irradiation for 30-60 s to polymerize MAOP-DMS. After solidification the droplets shrank by ca. 5-7% and acquired the shape shown in FIG. 24(b). The volume fraction of the disks reduced from 99.5 to 92.4%. FIG. 24(c) shows a typical SEM image of poly (MAOP-DMS) disks with aspect ratio 3.50. A highly periodic structure of the 2D lattice of droplets was preserved in the solid state. FIG. 25 shows the optical microscopy images of binary lattices generated in double orifice microfluidic device shown in FIG. 20.

Binary lattices were generated in a microfluidic device with a design shown in FIG. 20, following the schematic of FIG. 23. FIG. 25 shows exemplary lattices obtained from silicone oil and hexane droplets. Hexane droplets with undeformed diameter in the range from 95 to 400 μm contain a fluorescent dye and appear as dark. Droplet of silicone oil with undeformed diameter in the range from 90 to 250 μm from appear as lighter droplets. The continuous phase (L3) is formed by the aqueous sodium dodecylsulfate solution. By changing the flow rates of three liquids the structure of lattices could be carefully tuned. The flow rates of liquids played a three-fold role: they controlled the size of droplets, they determined the frequency of droplet generation, and they determined the packing ability of different populations of droplets in the downstream channel.

Figure 26A:
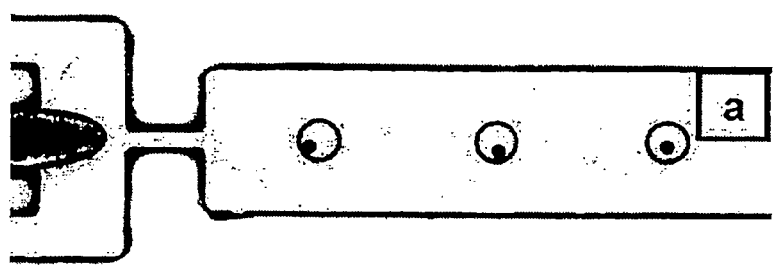
FIGS. 26(a-c) show the optical microscopy images of aqueous $TiO_2$ particles encapsulated within a monomer liquid, dispersed in an aqueous phase.
Figure 26B:
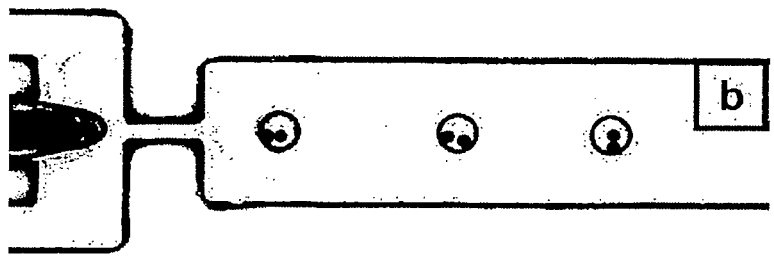
Figure 26C:
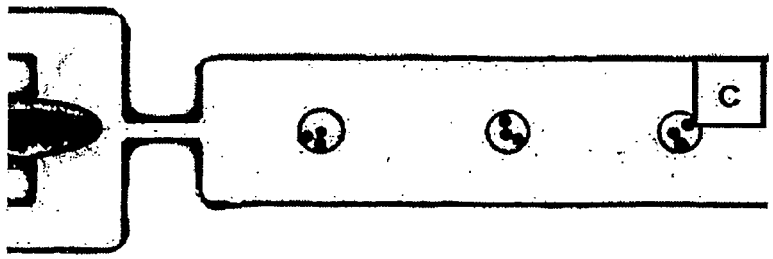

FIG. 26 shows the formation of core-shell droplets in the embodiment of the microfluidic device 201 in FIG. 20. An aqueous dispersion of $TiO_2$ with concentration 1-5 wt % was obtained in 2 wt % SDS or 0.1 wt % CTAB solution. This dispersion was supplied to the central channel (liquid A). A monomer TPGDA was supplied to the side channels (liquid B). Droplets of water encapsulating $TiO_2$ particles formed after forcing liquids A and B through the first orifice. Injection of the aqueous solution of SDS in concentration 2 wt % (Liquid C) through the outer channels and forcing liquids A, B, and C through the orifice led to the formation of TPGDA droplets encapsulating $TiO_2$ particles, dispersed in the aqueous SDS solution.

Two materials used for the fabrication of microfluidic reactors were Sylgard 184 PDMS (Dow Corning, typically used in soft lithography) and an elastomeric polyurethane copolymer. A typical composition of elastomeric polyurethane copolymer: (PU-5, weight ratio: AirthaneR PET 60D/poly (ethylene glycol), $M_n$=400/Glycerol 100/20.70/2.07). This polymer had transparency similar to Sylgard 184 PDMS (Dow Corning, typically used in soft lithography) and improved tensile strength and tear resistance. The mechanical properties and transparency of the polyurethane mold were close to those of PDMS; however, the contact angle of the SDS solution with the mold surface was 850, in contrast with a contact angle of 100°, measured on the PDMS surface.

Hydrophilic monomer droplets are produced and polymerized in a hydrophobic microfluidic reactors fabricated in poly (dimethyl siloxane). Nonpolar monomer droplets were produced and polymerized in polyurethane microfluidic reactors. The polyurethane polymer for fabricating microfluidic reactors is prepared by mixing one or more polyols with a number-average molecular weight 300 to 30,000 Daltons, with or one or more isocyanates with two or more functional groups and additives, comprising at least one crosslinker and at least one catalyst.

The polyol could be linear or branched polyether, i.e. polyalkylene oxides, produced by polyaddition of alkylene oxides, such as propylene oxide, ethylene oxide, butylene oxide, tetrahydrofuran, butylene oxide, epichlorohydrin, or styrene oxide with at least two functional hydroxyl groups. The polyurethane may have one polyol which is linear or branched polyester with at least two functional hydroxyl groups, a product obtained through the polycondensation of multifunctional carboxylic acids and hydroxyl compounds, or obtained through ring-open polymerization of cycloester.

The polyurethane may have one polyol is linear or branched polycarbonates with at least two functional hydroxyl groups, those that can be produced by reacting diols such as 1,4-butanediol and/or 1,6-hexanediol with diaryl carbonates, e.g., diphenyl carbonate, dialkyl carbonate, such as dimethyl carbonate or phosgene, with a number-average molecular weight of 800 to 5,000 daltons. The polyurethane can have polydiene polyol with at least two functional hydroxyl groups, and polydiene is polybutadiene and polyisoprene. The polyol may be hydrogenated polydiene polyol with at least two functional hydroxyl groups, and polydiene is polybutadiene and polyisoprene or their derivatives.

The polyol may be a polyolefin polyol with at least two functional hydroxyl groups, and polyolefin is polyethylene, polypropylene, polybutene, polyhexene, polyoctene and their copolymers. The polyol may be a polycycloolefin polyol with at least two functional hydroxyl groups. The polyol may be polysiloxane polyol with at least two functional hydroxyl groups, i.e. carbinol (hydroxyl) terminated polysiloxane, where the polysiloxane is homopolymer or copolymer containing siloxane units. The polyol may be a aliphatic polyol containing halogen such as fluoride, chloride, bromide with at least two functional hydroxyl groups, i.e. carbinol (hydroxyl) terminated fluorochemical polyol, which is homopolymer or copolymer containing fluorochemical units. The polyol may contain nitrogen, phosphate, silicon, sulfur, boron, metal elements, with at least two functional hydroxyl groups, i.e. carbinol (hydroxyl) terminated polyol.

As mentioned above, the polyurethane polymer for fabricating microfluidic reactors is prepared by mixing one or more polyols with a number-average molecular weight 300 to 30,000 daltons, or one or more isocyanates. The isocyanate may be a compound with two or more isocyanate groups in its molecule. The molecular backbone may be aromatic, aliphatic or cycloaliphatic.

The isocyanate may be toluene diisocyanate (TDI), diphenylmethane diisocyanate (MDI), naphthalene diisocyanate (NDI), phenylene diisocyanate (PDI), isophorone diisocyanate (IPDI), hexane diisocyanate (HDI), tetramethylene diisocyanate, hydrogenated diphenylemethane diisocyanate (methylenebis(cyclohexyl-4-isocyanate), HMDI), cyclohexylene diisocyanate, trimethylhexamthylene diisocyanate, triphenylmethane triisocynate, tetramethylene diisocyanate, methyl pentamethylene diisocyanate, dodecamethylene diisocyanate, 1-isocyanato-3,3,5-trimethyl-5-isocyanatomethyl cyclohexane, tris-(4-isocyanatophenyl)-thiophosphate, polymeric isocyanate. The isocynate may be a prepolymer containg at least two isocyanate groups, which is prepared from the isocynates listed above with polyols listed above and below or polyamines listed below, in non-stoichometric ratio.

The crosslinkers/chain extenders may be an aliphatic or aromatic polyol with a molecular weight of 70 to 500 and at least two hydroxyl groups. The polyol includes, but not limited, glycol, 1,4-butanediol, glycerol, trimethanol propane, anhydrosorbitol, castor oil and its derivatives, soybean oil and its derivatives, hydroquinone, bis(hydroxyethyl) hydroquinone, resorcinol, catechol, 2,2-bis(4-hydroxyphenyl)propane (bisphenol A).

The crosslinkers/chain extenders may be aliphatic or aromatic polyamines with a molecular weight of 70 to 500 and at least two amino groups as well as hydrazine or hydrazine hydrate. The polyamine may include diamino-diphenymethane, m-phenylene-diamine, 3,3'-dichloro-4,4'-diamino-diphenylmethane (MBOCA), 3,5-diamino-4-chloro-benzoat, diethyltoluene diamine (DETDA), 1,2-ethane diamine, 1,6-hexamethylene diamine, 1-amino-3,3,5-trimethyl-5-aminomethyl cyclohexane (isophorone diamine), piperazine, 1,4-diaminocyclohexane, bis(4-aminocyclohexyl)methane, adipic acid dihydrazide or diethylene triamine, N-(2-aminoethyl)-2-aminoethane sulfonic acid.

The catalyst may include nucleophilic catalysts such as amines, salts of weak acids, and electrophilic catalysts like organic metal compounds, and other catalysts like carboxylates, metal-chelates, hydrides, phosphines, quartenary ammonium, alcoholates. Other additives includes fillers, flame retardants, antiaging agents, colorants, plastizers, antioxidants, UV absorbing agents.

The polyurethane used in the microchannel may be radiation- or light-cured polyurethane oligomer/resin. The microchannel may be made using the protyping method of the designed master onto a substrate (wafer and glass) is exposing UV-cured resin, or compress molding. Polysiloxane or polyurethane microchannels may be formed by casting and then post-curing by condensation, or by UV-crosslinking. The suitable substrates may be made of silicon (wafer), glass and plastics, e.g., styrene copolymers such as ASA (acrylonitrile-styrene-acrylic ester) or ASA blends, ABS (acrylonitrile-butadiene-styrene), ABS blends, such as ABS polycarbonate, polycarbonate (PC) and PC/PBTP (polybutylene terephthalate), PA (polyamide)/ABS and polyurethanes produced by the RIM (=reaction injection molding) or RRIM (=reinforced RIM) process.

The surface of polysiloxane or polyurethane may be modified to improve its adhesion between the polymer and the substrate. The surface treatment is carried out by chemical agents, plasma, irradiation, light.

While the present invention has been described generally using a fluid containing a polymerizable constituent such as monomers, polymers and oligomers, and that the fluidic droplets polymerize, it will be appreciate that non-polymer based materials may be used. In such a case, the droplets harden during transit through the microfluidic channels. When the fluid contains polymeric or monomeric constituents, this hardening will generally be due to polymerization or physical crosslinking. The physical crosslinking process may include for example ionic crosslinking, hydrogen bonding, chelation or complexation. An example of ionic crosslinking is given for alginate microgels in FIG. 16, and such liquids can be alginate or chitosan.

When the process involves injection of three or more liquids into the microfluidic channel, particles with various shapes in addition to spheres, rods, discs, and ellipsoids can be produced. For example as shown in FIG. 14, other shaped particles such as plates, truncated spheres, hemispheres and bowls can be obtained by the process disclosed herein.

Particles can be obtained by introducing as a droplet phase polymer liquids that undergo reversible gelation: this liquids undergo shear thinning (i.e., reduction in viscosity) when forced into the orifice but after the formation of droplets they gel and form microgel particles.

The process of particle formation in the microfluidic reactors may occur in a series of sequential steps in the downstream portion of the microfluidic channel. When the droplets contain more than one polymerizable component one of them can harden (i.e., can be polymerized) by UV-irradiation) and the other one by a chemical process, which may or may not use catalysts, or by using a different type of irradiation, or by electrochemical processes.

The present process also allows one to make particles with interpenetrating networks: the chemical process (as in the previous claim) would not happen until we start the second process: UV-irradiation. Absorption of light and exothermic reaction increase temperature in the droplet and give rise to the chemical reaction. Thus two polymerizations occur simultaneously and result in interpenetrating polymer network. The speed of each reaction can control the morphology of the particles.

The present method may be configured as a continuous processes, that is, production of particles is done in a continuous throughput process in continuous miocrofluidic reactors. Alternatively, polymerization may be carried out after the particles exit the microfluidic device.

The present process provides a method of making lattices from a single population of droplets, or binary or multiple populations of droplets that differ in size and/or composition, as shown in FIGS. 24 and 25). These lattices may be hardened by polymerizing these droplets as in FIG. 24c, or a continuous phase.

The present process is also able to permit the encapsulation of selected constituents. For example, biological cells may be encapsulated in microgel (e.g. alginate) beads and one can control the number of cells that are placed in a bead.

With respect to the core/shell structures, the cores may be solid particles, for example polymer particles, or they may be liquid cores so that the core/shell structure is essentially a capsule, or solid or liquid cores which encapsulate other particles in the core and/or the shell of these core-shell particles (e.g., as in FIG. 26).

EXAMPLES

Example 1

Poly[tri(propylene glycol diacrylate)] microparticles were obtained in the microfluidic reactor with a design FIG. 1a with height 92 μm, orifice width 60 μm and the width of wavy channel 160 μm. An aqueous solution of 2 wt % sodium dodecylsulfate (SDS) was injected into the outer channels at a flow rate 2.0 mL/hr. The monomer tri(propylene glycol) diacrylate containing 4 wt % of photoinitiator 1-hydroxycyclohexyl phenyl ketone (HCPK) was injected at a flow rate 0.12 mL/hr into central channel. Following the formation of droplets the monomers were polymerized by exposing them to UV irradiation. The particle average size was 76 μm, and the polydispersity was 3%.

Example 2

Polymer polyTPGDA microrods were obtained in the microfluidic reactor with a design shown in FIG. 1a with height 92 μm, orifice width 60 μm and the width of wavy channel 160 μm. An aqueous solution of 2 wt % sodium dodecylsulfate (SDS) was injected into the outer channels at a flow rate 1.0 mL/hr. The monomer tri(propylene glycol) diacrylate containing 4 wt % of photoinitiator 1-hydroxycyclohexyl phenyl ketone (HCPK) was injected at a flow rate 0.40 mL/hr into central channel. Following the formation of droplets the monomers were polymerized by exposing them to UV-irradiation. The rods had an average length of 745 μm and an average width of 150 μm.

Example 3

Alginate microgels were obtained in the microfluidic reactor with a design shown in FIG. 16. The width of the outer and intermediate channels $W_c$ was 145 μm, width of the central channel $W_m$ is 50 μm. The width of orifice $W_o$ was from 50 μm. The width of the downstream channel $W_d$ varied from 600 μm. The widths $W_{L1}$ and $W_{L2}$ are 50 μm. An aqueous solution of alginate with the concentration from 0.1 wt % was introduced in the central microchannel (Fluid A, FIG. 16). An aqueous solution of the crosslinking agent calcium chloride with the concentration from 0.0.08 wt % was introduced in the two intermediate channels (Fluid B, FIG. 16). A mineral oil was introduced in the two outer channels (Fluid C, FIG. 16). The flow rates of alginate solution was 0.4 mL/hr, the flow rate of the solution of $CaCl_2$ is 0.2 mL/hr, the flow rate of the mineral oil is 2.2 mL/hr. The solutions of a biopolymer and of a crosslinking agent were mixed at the exit of the inner and intermediate channels and sheared by the mineral oil to form droplets after passing through the orifice. In the droplets alginate is ionically crosslinked with ions of $Ca^{2+}$ to produce microgel particles with diameter 25 μm and polydispersity 1.2%. The dispersion of microgel particles is collected at the exit of the downstream channel.

Example 4

Silicone oil (viscosity 50.0 cP) or dimethacrylate oxypropyldimethylsiloxane (viscosity 20 cP) was supplied to the outer channels of the microfluidic device shown in FIG. 1a. An aqueous 2 wt % solution of sodium dodecylsulfate was supplied to the central channel of the microfluidic device shown in FIG. 1a. The width of an orifice was 30 μm, the height and width of the downstream microchannel were 87±1.0 and 1000 μm, respectively. The flow rate of the aqueous phase was from 0.010 to 0.170 ml/hr; the flow rate of the oil phase was 0.02 mL/hr. The emulsification process was governed by the shear stress imposed on the droplet phase. The volume of droplets decreased with increasing Capillary number, $Ca=\mu v/\gamma$, where v is a characteristic velocity of the aqueous phase, $\gamma$ is the value of interfacial tension between the oil and aqueous fluids, $\gamma \approx 2.71$ mN/m,[13] and $\mu$ is viscosity of oil or monomer. The volume of droplets changed from $11 \times 10^{-6}$ to $2 \times 10^{-6}$ mL when the value of Ca increased from $1 \times 10^{-4}$ to $5 \times 10^{-4}$. The droplets with volume below $10.6 \times 10^{-6}$ mL had a size distribution (defined as standard deviation in droplet diameter d divided by mean diameter) below 3.0%. The velocity of droplets in the downstream channel of MFFD was slower than that of the continuous phase. Below $Ca=1.6 \times 10^{-4}$ the discoid droplets assembled into two-dimensional close-packed lattices filling the entire volume of the downstream microchannel. FIG. 24 shows typical optical microscopy images of the lattices of droplets of silicone oil.

Example 5

Droplets of dimethacrylate oxypropyldimethylsiloxane (viscosity 20 cP) mixed with 3.5±0.5 wt % of a photoinitiator 1-hydroxycyclohexyl phenyl ketone were generated as described in Example 4. A lattice of discoid droplets of dimethacrylate oxypropyldimethylsiloxane generated under flow rates of dimethacrylate oxypropyldimethylsiloxane 0.0030 ml/hr and flow rate of aqueous phases 0.1000 ml/hr. The array of droplets was photopolymerized by exposing it to UV irradiation 30-180 s to the UV-light (UV lamp, UVAPRINT 40 C/CE, Dr. K. Hönle GmbH UV-Technologie with an output of 400 W at a wavelength of 330-380 nm). FIG. 24(a) and (b) shows the lattice of discoid disks before and after polymerization, respectively. FIG. 24(c) shows a typical scanning microscope image lattices of poly(dimethacrylate oxypropyldimethylsiloxane) disks with aspect ratio 3.50 following monomer polymerization. Following polymerization the volume fraction of the disks reduced from 99.5 to 92.4%.

Example 7

Binary lattices were generated in a microfluidic device with a design shown in FIG. 20. The height of the microfluidic device was 95 to 100 μm. The width of the first orifice was 40 μm, the width of the second orifice was 50 μm. The width of the first outlet was outlet (down stream channel was 170 μm, the width of the second downstream channel was 430 μm.

Figure 25A:
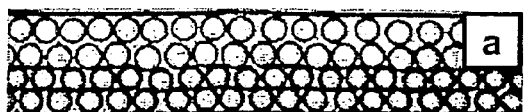
FIG. 25 shows the optical microscopy images of gliding two-dimensional lattices obtained from two populations of droplets produced in the double-orifice microfluidic device in FIG. 20.
Figure 25B:
Figure 25C:
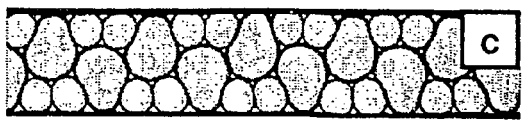
Figure 25D:

Silicone oil (viscositiy 10 cP) was inserted in the central channel, an aqueous solution of sodium dodecylsulfate was supplied to the outer channels. When the two liquids were forced through the first orifice a thread of silicone oil broke up in dropets following mechanism shown in schematic of FIG. 21a. Droplets of silicone oil with diameter from 115 to 220 μm were formed, dispersed in the aqueous continuous phase. This dispersion was forced through the second orifice, simultaneously with hexane added to the first outlet through the side channels. When three liquids were forced through the second orifice hexane thread broke up in droplets following the mechanism shown schematically in FIG. 21c. The diameter of hexane droplets was from 95 to 400 μm. In the second downstream channel the droplets of silicone oil and hexane packed in binary lattices with a high degree of order and symmetry. FIG. 25 shows exemplary lattices obtained from silicone oil and hexane droplets. The flow rates of an aqueous phase/hexane/silicone oil are: 0.6/0.4/0.4 (FIG. 25a); 0.1/0.1/0.2 ml/h (FIG. 25b); 0.4/0.6/0.4 ml/h (FIG. 25c); and 0.1/0.1/0.01 ml/h (FIG. 25d).

Example 8

Biocompatible copolymer particles of poly[(ethylene glycol) phenyl ether acrylate-pentaerythritol triacrylate] were obtained in the microfluidic reactor as in FIG. 1 with height 92 μm and orifice width 60 μm. An aqueous 2 wt % solution of sodium dodecylsulfate was injected into the outer channels at a flow rate 4.0 mL/hr. A mixture of ethylene glycol) phenyl ether acrylate and pentaerythritol triacrylate (weight ratio of 9/1) containing 4 wt % of photoinitiator 2-hydroxy-2-methylpropiophenone was injected at a flow rate 0.10 mL/hr into central channel. Following the formation of droplets the monomers were polymerized by exposing them to UV irradiation. The size of microspheres was 70 μm, polydispersity of particles was 1.5%.

Example 9

We used a microfluidic flow-focusing device in FIG. 5 to obtain polyTPGDA capsules with a single core. The rectangular orifice with a cross was section was placed a distance $H_f$=400 μm downstream of five coaxial inlet streams of liquids. The width of the orifice was D=60 μm. The total width of the upstream channel was $W_u$=1300 μm. The width of downstream channel was $W_d$=650 μm. The width of the central channel is $W_o$=100 μm, the width of two intermediate channels is $W_m$=150 μm. The width of the two outer channels is $W_w$=150 μm. The uniform depth of the channels is 200 μm.

Three immiscible liquids: a silicon oil (SO, viscosity 10 cSt) mixed with 0.2 wt % of surfactant sorbitan monooleate SPAN 80, tripropyleneglycol diacrylate (TPGDA) comprising 4 wt % of photoinitiator 1-hydroxycyclohexyl phenyl ketone (HCPK), and a 2 wt % aqueous solution of sodium dodecylsulfate were supplied to the central, intermediate and outer channels of the microfluidic device, respectively. The flow rate of the oil phase was 0.045 mL/hr. The flow rate of the monomer phase was 0.30 mL/hr. The flow rate of the aqueous phase was 52.0 mL/hr.

Figure 14A:
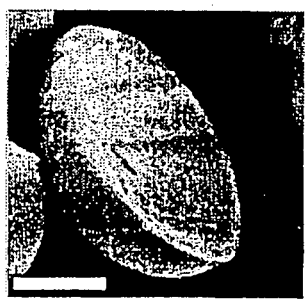
FIGS. 14a-e show particles obtained from the droplets obtained in regions A, B, C, and D, respectively, of the ternary diagram of FIG. 13.
Figure 14B:
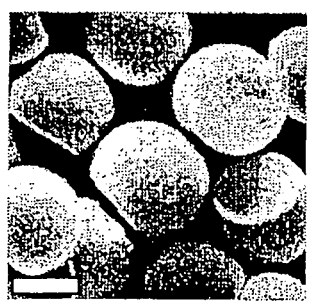
Figure 14C:
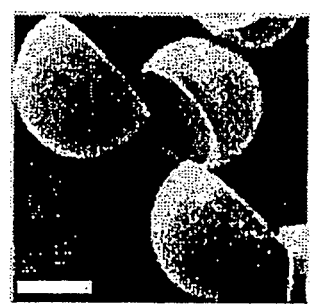
Figure 14D:
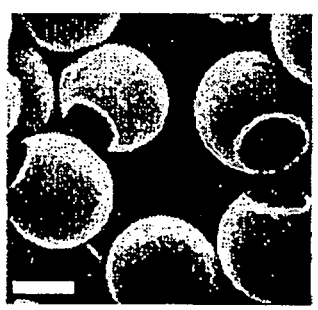
Figure 14E:
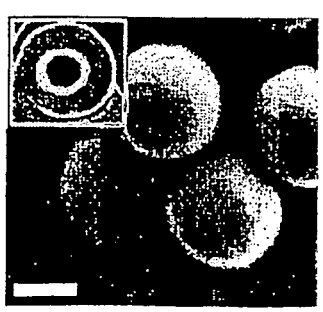
Figure 14F:
FIG. 14f shows microspheres with three cores obtained by polymerizing droplets in region 1.

Under these conditions monomer droplets with a single core were formed. Upon polymerization polyTPGDA capsules were obtained with single oil core (FIG. 14e). The diameter of capsules was 60 μm, polydispersity was 1.8%.

Example 10

We used a microfluidic flow-focusing device in FIG. 5 to obtain polyTPGDA capsules with multiple cores. The microfluidic reactor, liquids and the configuration of the experiment were as in Example 9. The flow rate of the oil phase was 0.052 mL/hr. The flow rate of the monomer phase was $Q_m$=0.11 mL/hr. The flow rate of the aqueous phase was 24 mL/hr.

TPGDA capsules with multiple oil cores were produced by breaking up a coaxial TPGDA/oil jet obtained at silicone oil flow rate of 0.05 mL/hr, monomer, flow rate of 0.32 mL/hr and 2 wt % aqueous solution of sodium dodecylsulfate flow rate of 24.0 mL/hr. in the outer channels.

The monomer in TPGDA/silicone oil capsules was photopolymerized by exposing the droplets to UV-irradiation. Typically particle diameter was from 40 to 70 μm, with polydispersity below 2.3%.

Example 11

PolyTPGDA plates were obtained in the microfluidic device with a design shown in FIG. 5. The microfluidic reactor, liquids and the configuration of the experiment were as in Example 9. Silicone oil (viscosity 10 cSt) mixed with 0.2 wt % Span-80 was injected at a flow rate of 0.2 mL/hr, tri(propylene glycol) diacrylate mixed with 4 wt % of 1-hydroxycyclohexyl phenyl ketone had a total flow rate of 0.05 mL/hr, a 2 wt % aqueous solution of sodium dodecylsulfate had a total flow rate of 12.0 mL/hr. The droplets formed by silicone oil and TPGDA phases were exposed to UV-irradiation and a monomer was polymerized. The silicone oil was then removed with acetone. FIG. 14a shows a typical SEM image of polyTPGDA plate. The height of plates was 35 μm, with a diameter of 135 μm.

Example 12

TPGDA droplets with water cores encapsulating various number of $TiO_2$ particles were obtained in the microfluidic reactor with a design shown in FIG. 20. The width of the two orifices and the height of the microfluidic reactor were 40.0 and 65.3 ∞m, respectively. The reactor was fabricated in polyurethane elastomer. An dispersion of $TiO_2$ with concentration 5% in 0.1 wt % aqueous cetyl trimethyl ammonium bromide solution was supplied to the central channel at a flow rate is 0.01 ml/h. TPGDA was supplied to the outer channels at a flow rate 0.10 ml/h. Monodisperse aqueous droplets containing $TiO_2$ particles were formed when an aqueous and a monomer liquids were forced into a narrow orifice. Following injection of 2 wt % sodium dodecylsulfate solution at a flow rate 4.00 ml/h and passage of three liquids through the second orifice core-shell droplets were formed comprising an aqueous core with $TiO_2$ particles, and a TPGDA shell, dispersed in a continuous phase formed by an aqueous 2 wt % sodium dodecylsulfate solution.

In summary, the present invention provides a method methodology which opens a new avenue in producing polymer particles with different dimensions, compositions, shapes and structures. For the first time as disclosed herein it has been shown that it is possible to synthesize particles with shapes that cannot easily and reproducibly produced in conventional polymer synthesis. Since a typical area of the microfluidic channels is c.a. 2×5 cm, a glass plate with the size of 8×5 cm can accommodate up to four microfluidic reactors yielding polymerization with higher efficiency or the possibility to employ a combinatorial approach in particle synthesis with microfluidic reactors resulting in increased yield of the process or the possibility to employ a combinatorial approach in particle synthesis.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A process for producing core/shell droplets, the process comprising:
    providing a microfluidic device comprising
        at least five microfluidic inlets, including a central microfluidic channel inlet, two inner microfluidic channel inlets, and two outer microfluidic channel inlets, wherein the inner microfluidic channel inlets are arranged on both sides of the central microfluidic channel inlet, and wherein the outer microfluidic channel inlets are arranged adjacent to the inner microfluidic channel inlets;
        an orifice in fluid communication with the at least five microfluidic inlets; and
        a microfluidic channel in fluid communication with the orifice;
    injecting a first fluid into the central microfluidic channel inlet, a second fluid into the inner microfluidic channel inlets, and a third fluid into the outer microfluidic channel inlets, wherein neighbouring fluids are immiscible;
    flowing the first fluid, second fluid, and third fluid through the orifice and into the microfluidic channel, such that the second fluid surrounds the first fluid to form a coaxial stream within the third fluid; and
    controlling relative flow rates of each of the first fluid, second fluid, and third fluid, such that during passage of the coaxial stream through the microfluidic channel, the coaxial stream breaks up into segments, thereby forming core/shell fluidic droplets with one or more fluidic cores of the first fluid enveloped by a shell of the second fluid.

2. The process according to claim 1 wherein at least the second fluid comprises a constituent which can harden, and wherein the microfluidic channel is sufficiently long so that at least the shell of each droplet hardens while flowing through the channel, thereby forming core/shell microparticles.

3. The process according to claim 2 wherein the constituent which can harden is hardened by any one of ionic crosslinking, hydrogen bonding, chelation, complexation and combinations thereof.

4. The process according to claim 2 wherein the constituent that can harden comprises a polymerizable constituent, and wherein said shells harden by polymerizing into polymer particles.

5. The process according to claim 1 wherein the microfluidic channel is constructed and configured to produce fluidic droplets having a pre-selected size and or shape.

6. The process according to claim 1 wherein the microfluidic channel has a cross-sectional shape being any one of circular, oval, triangular, irregular, square, and rectangular.

7. The process according to claim 1 wherein the microfluidic channel has an aspect ratio (length to average cross sectional dimension) of at least about 10:1.

8. The process according to claim 1 wherein a diameter of the fluidic droplets is controlled by controlling one or more of flow rates and flow rate ratios of the fluids, dimensions of said microfluidic channel, properties of the fluids including viscosity and interfacial tension between the fluids, and wherein said microfluidic channel is constructed with pre-selected cross-sectional shape and dimensions to give a desired shape to said fluidic droplets upon transit of said fluidic droplets through said microfluidic channel.

9. The process according to claim 2 wherein said fluidic droplets have a diameter d, and wherein the microfluidic channel is constructed with pre-selected cross-sectional shape and dimensions selected so that d is larger than at least one of the dimensions of the microfluidic channel so that fluidic droplets with non-spherical shapes are formed upon transit through the microfluidic channel with pre-selected cross-sectional shape and dimensions so that microparticles have a non-spherical shape.

10. The process according to claim 9 wherein an aspect ratio for said non-spherical droplets is varied by changing a ratio between fluidic droplet volume and said dimensions of the microfluidic channel.

11. The process according to claim 2 wherein said droplets have a diameter d, and wherein a portion of the microfluidic channel has a width w and a height h, and wherein when said portion of the microfluidic channel is constructed so that $w > d$ and $h > d$, and a flow rate of the droplets through the microfluidic channel is selected to be slow enough so that the microparticles maintain a spherical shape.

12. The process according to claim 2 wherein said fluidic droplets have a diameter d, and wherein a portion of the microfluidic channel has a width w and a height h, and wherein when said portion of the microfluidic channel is constructed so that $w > d$ and $h > d$, and a flow rate of the fluidic droplets through the microfluidic channel is selected to be high enough so that the microparticles acquire an ellipsoidal shape.

13. The process according to claim 2 wherein said fluidic droplets have a diameter d, and wherein a portion of the microfluidic channel has a width w and a height h, and wherein when said portion of the microfluidic channel is constructed with $w > d$ and $h < d$ so that the microparticles acquire a discoid shape.

14. The process according to claim 2 wherein said droplets have a diameter d, and wherein a portion of the microfluidic channel has a width w and a height h, and wherein when said portion of the microfluidic channel is constructed with $w < d$, $h < d$ so that the microparticles acquire a rod shape.

15. The process according to claim 1 comprising adjusting a flow rate ratio of each of the first fluid, second fluid, and third fluid to selectively control at least one of size of the cores, a thickness of shells, a size of core-shell fluidic droplets, a number of cores per fluidic droplet.

16. The process according to claim 1 wherein the fluid injected into the two inner microfluidic channel inlets is an oil, and wherein the fluid injected into the two outer microfluidic channel inlets is an aqueous fluid.

17. The process according to claim 1 wherein said coaxial stream is unstable to perturbations with wavelengths larger than a circumference of said coaxial stream which causes the coaxial stream to break up into segments.

18. The process according to claim 1, including controlling a number of cores per fluid droplet by adjusting relative flow rates of the first fluid, second fluid, and third fluid by varying interfacial capillary wavelengths $\lambda_m$ and $\lambda_o$, where $\lambda_m$ is an interfacial capillary wavelength of said first fluid, and $\lambda_o$ is an interfacial capillary wavelength of said second fluid.

19. The process according to claim 2 wherein the constituent which can harden comprises a mixture of two or more monomers, oligomers, liquid polymers or combinations thereof such that said microparticles are copolymer particles.

20. The process according to claim 2 wherein the constituent which can harden comprises a liquid polymer.

21. The process according to claim 1 wherein said microfluidic channel is formed in a microreactor.

22. The process according to claim 21 wherein said microreactor comprises a hydrophilic material.

23. The process according to claim 21 wherein said microreactor comprises a hydrophobic material.

24. The process according to claim 2, wherein said first fluid comprises a constituent selected from the group consisting of organic dyes, chromophores, nonlinear optical compounds, fluorescent dyes, inorganic chemicals, inorganic particles, inorganic pigments, fluorescent inorganic particles, semiconductor nanoparticles, quantum dots, inorganic particles having pre-selected magnetic properties, inorganic particles having pre-selected anti-magnetic properties, inorganic particles having pre-selected electrically conductive and/or semiconducting properties, carbon nanotubes, and liquid crystals, wherein the constituent is incorporated into said microparticles wherein said microparticles are composite hardened particles.

25. The process according to claim 2 wherein said microparticles are monodisperse.

26. The process according to claim 25 wherein no more than approximately 5% of the microparticles have a diameter greater than approximately 5% of the average diameter of all microparticles.

27. The process according to claim 25 wherein no more than approximately 3% of the microparticles have a diameter greater than approximately 10% of the average diameter of all microparticles.

28. The process according to claim 2, wherein the microparticles have an average diameter of less than about 100 micrometers.

29. The process according to claim 2, wherein the microparticles have a shape selected from the group consisting of spherical, disk, rod, oval, ellipsoidal, plates, truncated spheres, hemispheres and bowls.

30. The process according to claim 2, wherein the microparticles are hollow.

31. The process according to claim 2, wherein the microparticles with a core/shell structure have a controlled number of cores.

32. The process according to claim 2, wherein the first fluid further comprises a polymerizable constituent including carbon or carbon-wall nanotubes so that the microparticles are polymer particles having carbon or carbon-wall nanotubes incorporated therein.

33. The process according to claim 2, wherein said first fluid further comprises an unpolymerizable liquid wherein some of said unpolymerizable liquid for producing polymer microparticles having unpolymerizable liquids incorporated into the microparticles.

34. The process according to claim 33, wherein the unpolymerizable liquid is any one of a liquid crystal, a porogen, a dispersion of inorganic or organic particles.

35. The process according to claim 1, wherein said first fluid comprises two or more monomers.

36. The process according to claim 2, wherein said first fluid comprises a biocompatible product including one or more of starch, derivatives, polymers containing 3-hydroxybutyrate and its derivatives, polymers containing 3-hydroxyvalerate and its derivatives, protein, nucleic acids (DNA, RNA), amino acid (peptide), liposomes, agarose and its derivatives, chitosan and its derivatives, alginate and its derivatives, pectin and its derivatives, cellulose derivatives, drugs and their derivatives which are incorporated into said microparticles wherein said microparticles are composite particles.

37. The process according to claim 1 including exposing said fluidic droplets in said microfluidic channel to a polymerizing agent for polymerizing said fluidic droplets.

38. The process according to claim 37 wherein said polymerizing agent is one of heat, ultra-violet light (UV), plasma, irradiation.

39. The process according to claim 1 further comprising exposing said fluidic droplets in said microfluidic channel to an external field selected from the group consisting of a magnetic field, an electric field, light, radiation and combinations thereof.

40. The process according to claim 1 wherein said first fluid includes a gel precursor material that hardens upon chemical or physical crosslinking so that upon hardening the fluidic droplets gel to form microgel particles.

41. The process according to claim 2 wherein said first fluid includes biological cells so that said microparticles contain biological cells.

42. The process according to claim 1 wherein said first fluid comprises two or more monomeric, polymeric or oligomeric constituents, and wherein the fluidic droplets harden in a stepwise manner, the process further comprising exposing said fluidic droplets to polymerizing agents at different positions along said microfluidic channel in a pre-selected sequence to sequentially polymerize the different constituents at different times.

43. The process according to claim 2 wherein production of microparticles is done in a continuous throughput process.

44. The process according to claim 2 wherein the microparticles include cores that are solid.

45. The process according to claim 2 wherein the microparticles include cores are liquids encapsulated by said shell.

46. The process according to claim 1 further comprising forming a two-dimensional lattice of droplets within the microfluidic channel.

47. The process according to claim 2, wherein the microparticles are porous.

48. The process according to claim 1 wherein said microfluidic channel is formed in a microfluidic reactor made of a polyurethane material.

* * * * *

UNITED STATES PATENT AND TRADEMARK OFFICE
CERTIFICATE OF CORRECTION

PATENT NO. : 8,696,952 B2  
APPLICATION NO. : 11/587251  
DATED : April 15, 2014  
INVENTOR(S) : Eugenia Kumacheva et al.

Page 1 of 1

It is certified that error appears in the above-identified patent and that said Letters Patent is hereby corrected as shown below:

On the Title Page, Item (60)

Provisional application No. 60/564,614, should be corrected to show a filing date of Apr. 23, 2004.

Signed and Sealed this
Twenty-fourth Day of June, 2014

Michelle K. Lee
*Deputy Director of the United States Patent and Trademark Office*